(12) United States Patent
Saxena et al.

(10) Patent No.: US 11,542,473 B2
(45) Date of Patent: Jan. 3, 2023

(54) METHODS AND COMPOSITIONS FOR GENERATING HEMATOPOIETIC CELLS

(71) Applicant: Amniotics AB, Lund (SE)

(72) Inventors: Shobhit Saxena, Shahjahanpur (IN);
Roger Emanuel Rönn, Täby (SE);
Niels-Bjarne Woods, Furulund (SE)

(73) Assignee: Amniotics AB, Lund (SE)

( * ) Notice: Subject to any disclaimer, the term of this patent is extended or adjusted under 35 U.S.C. 154(b) by 579 days.

(21) Appl. No.: 16/343,617

(22) PCT Filed: Oct. 21, 2016

(86) PCT No.: PCT/IB2016/001628
§ 371 (c)(1),
(2) Date: Apr. 19, 2019

(87) PCT Pub. No.: WO2018/073615
PCT Pub. Date: Apr. 26, 2018

(65) Prior Publication Data
US 2020/0048609 A1    Feb. 13, 2020

(51) Int. Cl.
*C12N 5/0789* (2010.01)

(52) U.S. Cl.
CPC ........ *C12N 5/0647* (2013.01); *C12N 2501/01* (2013.01); *C12N 2502/088* (2013.01); *C12N 2506/02* (2013.01); *C12N 2506/03* (2013.01); *C12N 2506/11* (2013.01)

(58) Field of Classification Search
CPC .............. C12N 5/0647; C12N 2501/01; C12N 2506/11
See application file for complete search history.

(56) References Cited

U.S. PATENT DOCUMENTS

| | | |
|---|---|---|
| 4,308,875 A | 1/1982 | Young |
| 4,567,882 A | 2/1986 | Heller |
| 4,787,894 A | 11/1988 | Turnbull |
| 5,019,039 A | 5/1991 | Anderson |
| 5,048,530 A | 9/1991 | Hurwitz |
| 5,100,387 A | 3/1992 | Ng |
| 5,395,379 A | 3/1995 | Deutchman et al. |
| 5,494,044 A | 2/1996 | Sundberg |
| 5,951,497 A | 9/1999 | Wallace et al. |
| 6,378,523 B1 | 4/2002 | Christopher |
| 6,461,628 B1 | 10/2002 | Blanchard et al. |
| 6,479,064 B1 | 11/2002 | Atala |
| 6,506,574 B1 | 1/2003 | Rambhatla et al. |
| 6,733,433 B1 | 5/2004 | Fell |
| 7,255,879 B2 | 8/2007 | Hariri |
| 7,311,905 B2 | 12/2007 | Hariri |
| 7,596,385 B2 | 9/2009 | Aghvami et al. |
| 7,638,141 B2 | 12/2009 | Hariri |
| 7,682,803 B2 | 3/2010 | Paludan et al. |
| 7,802,574 B2 | 9/2010 | Schultz |
| 7,914,779 B2 | 3/2011 | Hariri |
| 8,987,203 B2 | 3/2015 | Van Leeuwen et al. |
| 9,868,939 B2 | 1/2018 | Slukvin et al. |
| 10,073,096 B2 | 9/2018 | Lakshmipathy et al. |
| 10,143,448 B2 | 12/2018 | Brunner |
| 10,201,620 B2 | 2/2019 | Meis et al. |
| 10,983,123 B2 | 4/2021 | Lakshmipathy et al. |
| 2005/0042595 A1 | 2/2005 | Haas |
| 2005/0054093 A1 | 3/2005 | Haas |
| 2005/0059152 A1 | 3/2005 | Tanavde et al. |
| 2005/0124003 A1 | 6/2005 | Atala et al. |
| 2005/0148074 A1 | 7/2005 | Davies et al. |
| 2007/0134210 A1 | 6/2007 | Heidaran |
| 2007/0243172 A1 | 10/2007 | Ra et al. |
| 2007/0298497 A1 | 12/2007 | Antwiler |
| 2009/0191159 A1 | 7/2009 | Sakurada et al. |
| 2010/0113327 A1 | 5/2010 | Van Leeuwen et al. |
| 2010/0124569 A1 | 5/2010 | Abbot et al. |
| 2010/0136679 A1 | 6/2010 | Min et al. |
| 2010/0323446 A1 | 12/2010 | Barnett et al. |

(Continued)

FOREIGN PATENT DOCUMENTS

| | | |
|---|---|---|
| AU | 2014201181 | 3/2014 |
| CN | 1407088 | 4/2003 |

(Continued)

OTHER PUBLICATIONS

Saxena ,2016, Stem Cell Reports, 6:692-703 (Year: 2016).*
Saxena (Stem Cell Reports, 6:692-703).*
Goichberg (2006, Blood, 107:870-879).*
Halliwell (2014, Biomed J, 37:99-105).*
Forman (2002, Am J Respir Crit Care Med, 166:54-58).*
Dewar (2003, Leukemia, 17:1713-1721).*
Anker et al., "Isolation of Mesenchymal Stem Cells of Fetal or Maternal Origin from Human Placenta," Stem Cells, vol. 22, 2004, p. 1338-1345.
Allard et al., "Immunohistochemical Toolkit for Tracking and Quantifying Xenotransplanted Human Stem Cells." Regenerative Medicine 9.4 (2014): 437-452.

(Continued)

*Primary Examiner* — Valarie E Bertoglio
(74) *Attorney, Agent, or Firm* — Knobbe, Martens, Olson & Bear, LLP

(57) ABSTRACT

Maturation signals provided via cyclic adenosine monophosphate (cAMP)/Exchange proteins activated by cAMP (Epac) signaling during in vitro generation of blood cells from reprogrammed cells or pluripotent stem cells achieve superior function of hematopoietic cells differentiated from stem cells. The cAMP/Epac signaling enables an increased efficiency of production of precursor to blood and to blood cells. These generated blood cells can be utilized for therapeutics, treatments, disease prevention, drug discovery, personalized medicine, regenerative medicine, cell and tissue generation, universal donor banks and related methods and compositions.

20 Claims, 19 Drawing Sheets
Specification includes a Sequence Listing.

(56) References Cited

U.S. PATENT DOCUMENTS

| | | |
|---|---|---|
| 2011/0256110 A1 | 10/2011 | Perin et al. |
| 2012/0142102 A1 | 6/2012 | Chen et al. |
| 2012/0190731 A1 | 7/2012 | Messina |
| 2013/0157353 A1 | 6/2013 | Dijkhuizen Borgart et al. |
| 2013/0171110 A1 | 7/2013 | Woods et al. |
| 2014/0038291 A1 | 2/2014 | Ahlfors et al. |
| 2014/0369968 A1 | 12/2014 | Slukvin et al. |
| 2015/0247852 A1 | 9/2015 | Lakshmipathy et al. |
| 2016/0030489 A1 | 2/2016 | Larsson et al. |
| 2016/0068815 A1 | 3/2016 | Larsson et al. |
| 2016/0199413 A1 | 7/2016 | Simonson et al. |
| 2018/0059109 A1 | 3/2018 | Hsuan et al. |
| 2018/0119104 A1 | 5/2018 | Slukvin et al. |
| 2019/0064164 A1 | 2/2019 | Lakshmipathy et al. |
| 2020/0056156 A1 | 2/2020 | Ino et al. |
| 2020/0095551 A1 | 3/2020 | Woods et al. |
| 2020/0171097 A1 | 6/2020 | Larsson et al. |

FOREIGN PATENT DOCUMENTS

| | | | |
|---|---|---|---|
| CN | 202569006 | 12/2012 | |
| CN | 202723948 | 2/2013 | |
| CN | 109777773 A | 5/2019 | |
| CN | 109971709 A | 7/2019 | |
| DE | 202004012970 | 12/2005 | |
| EP | 2302036 | 3/2011 | |
| EP | 2479261 | 7/2012 | |
| EP | 3029137 | 1/2019 | |
| EP | 3117828 | 2/2020 | |
| JP | 2005323534 | 11/2005 | |
| JP | 2010529851 | 9/2010 | |
| JP | 2010265220 | 11/2010 | |
| JP | 2011084566 | 4/2011 | |
| JP | 2012521780 | 9/2012 | |
| JP | 2012255025 | 12/2012 | |
| WO | WO 0235992 | 5/2002 | |
| WO | WO 03042405 | 5/2003 | |
| WO | WO 03068937 | 8/2003 | |
| WO | WO 05078073 | 8/2005 | |
| WO | WO 06012404 | 2/2006 | |
| WO | WO 2008/060139 | 5/2008 | |
| WO | WO 2009/031818 | 3/2009 | |
| WO | WO 2009/052132 | 4/2009 | |
| WO | WO 2009/135206 A1 | 11/2009 | |
| WO | WO 10099539 | 9/2010 | |
| WO | WO 2012/021845 | 2/2012 | |
| WO | WO-2012021845 A2 * | 2/2012 | ............... A61P 3/00 |
| WO | WO 2012/070032 | 5/2012 | |
| WO | WO 2013/082487 | 6/2013 | |
| WO | WO 2014/055121 | 4/2014 | |
| WO | WO 2014/140913 | 9/2014 | |
| WO | WO 2015/016761 | 2/2015 | |
| WO | WO 2015/023720 | 2/2015 | |
| WO | WO 2015/073786 | 5/2015 | |
| WO | WO 2016/120310 | 8/2016 | |
| WO | WO-2016120310 A1 * | 8/2016 | ........... A61K 31/522 |
| WO | WO 2018/073615 | 4/2018 | |
| WO | WO 2018/083700 | 5/2018 | |
| WO | WO 2018/169554 | 9/2018 | |
| WO | WO 2018/185584 | 10/2018 | |
| WO | WO 2018/186421 | 10/2018 | |
| WO | WO 2019/035880 | 2/2019 | |
| WO | WO 2019/104381 A1 | 6/2019 | |
| WO | WO 2021/087436 | 5/2021 | |

OTHER PUBLICATIONS

Bar-Nur et al., "Epigenetic Memory and Preferential Lineage-Specific Defferentation in Induced Pluripotent Stem Giles Derived from Human Pancreatic Isley Bets Cells", Cell Stem Cell vol. 9, No. 1, 2011, pp. 17-23.

Bieback et al., "Clinical Protocols foe the Isolation and Expansion of Mesenchymal Stromal Cells", Transfucion Medicine and Hemotherapy, 2008, vol. 35, pp. 286-294. (Year: 2008).

Bongso et al., "Taking Stem Cells to the Clinic: Major Challenges," Journal of Cellular Biochemistry, vol. 105, 2008, p. 1352-1360.

Bottai et al., "Third trimester amniotic fluid cells with the capacity to develop neural phenotypes and with heterogeneity among subpopulations," Restorative Neurology and Neuroscience, vol. 30, 2012, p. 55-68.

Bossolasco et al., "Molecular and phenotypic characterization of human amniotic fluid cells and their differentiation potential", Cell Research, 2006 16: pp. 329-336.

Cao et al., Stem Cell Repair of Central Nervous System Injury Neuroscience Res vol. 68, 2002, pp. 501-510.

Carette et al., "Generation of iPSCs from cultured human malignant cells", Blood, vol. 115, No. 20, 2010, pp. 4039-4042.

Chanda et al., "Retinoic Acid Signaling Is Essential for Embryonic Hematopoietic Stem Cell Development", Cell, vol. 155, No. 1, Sep. 26, 2013, pp. 215-227, XP028729738, ISSN: 0092-8674, DOI: 10.1016/J.CELL.2013.08.055.

Cipolleschi et al ("The Role of Hypoxia in the Maintenance of Hematopoietic Stem Cells," Blood, vol. 82, No. 7 (Oct. 1, 1993: pp. 2031-2037).

De Coppi, et al., "Isolation of Amniotic Stem Cell Lines with Potential for Therapy". Nature Biotechnology vol. 25, No. 1 (2007) 100-106.

Dewar et al. "Imatinib inhibits the in vitro development of the monocyte/macrophage lineage from normal human bone marrow progenitors" Leukemia (2003) vol. 17 pp. 1713-1721.

de Wynter et al., "Comparison of Purity and Enrichment of CD34 + Cells from Bone marrow, Umbilical Cord and Peripheral Blood (primed for Apheresis) Using Five Separation Systems", Stem Cells, 1995, vol. 13, pp. 524-532.

Djouad, et al., "Mesenchymal Stem Cells: Innovative Therapeutic Tools for Rheumatic Diseases." Nature Reviews Rheumatology 5.7 (2009): 392-399.

Dobreva et al., "On the origin of amniotic stem cells: of mice and men," The International Journal of Developmental Biology, vol. 54, 2010, p. 761-777.

Eggerman J et al., "Endothelial progenitor cell culture and differentiation in vitro: a methodological comparison using human umbilical cord blood", Cardiovascular Research, Oxford University Press, GB, vol. 58, No. 2, May 1, 2003 (May 1, 2003), pp. 478-486, XP002351441, ISSN: 0008-6363, DOI: 10.1016/30008-6363(03)00252-9 002351441 I.

Forman et al., Reactive Oxygen Species and Cell Signaling, Respiratory Burst in Macrophage Signaling vol. 166 pp. 54-58, 2002.

Forraz et al., "The umbilical cord: a rich and ethical stem cell source to advance regenerative Medicine," Cell Proliferation, vol. 44, 2011, p. 60-69.

Friedman et al., "Umbilical Cord Mesenchymal Stem Cells: Adjuvants for Human Cell Transplantation," American Society for Blood and Marrow Transplantation, vol. 13, 2007, p. 1477-1486.

Ge et al. "The Size of Mesenchymal Stem Cells is a Significant Cause of Vascular Obstructions and Stroke". Stem Cell Reviews and Reports, Apr. 2014.10(2): 295-303.

Ghosh et al., "Persistnat Donor Cell Gene Expression among Human Induced Pluripotent Stem Cells Contributes to Differences with Human Embryonic Stem Cells", Plos One, vol. 5, No. 2, 2010, p. E8975.

Halliwell, "Cell Culture, Oxidative Stress, and Antioxidants: Avoiding Pitfalls", Biomed J. vol. 37, No. 3, May-Jun. 2014.

Hamid et al., "Highly potent stem cells from full-term amniotic fluid: A realistic perspective" Reprod Biol, 2017, 17(1):9-18; whole document.

Han et al., "Genetically modified mesenchymal stem cell therapy for acute respiratory distress syndrome", stem Cell Res Ther, 2019, 10(1 ):386; whole document.

Hanna et al., "Direct cell reprogramming is a stochastic process amenable to acceleration"., Nature vol. 462, No. 7273, 2009, pp. 595-601.

Hoogduijn et al., "Morphology and Size of Stem Cells From Mouse and Whale: Observational Study." Bmj 347 (2013).

Ikehata et al. "Environmenatal Molecular Mutagenesis", vol. 41, No. 4, 2003, pp. 280-292.

(56) References Cited

OTHER PUBLICATIONS

Ikehata et al., "Mutation spectrum in sunlight-exposued", vol. 556, No. 1-2, 2004, pp. 11-24.
Ingram D A et al., "Identification of a novel hierarchy of endothelial progenitor cells using human peripheral and umbilical cord blood", Blood, American Society of Hematology, US, vol. 104, No. 9, Nov. 1, 2004 (Nov. 1, 2004), pp. 2752-2760, XP002351443, ISSN: 0006-4971, DOI: 10.1182/Blood-2004-04-1396 002351443 X.
Kim et al., "Epigenetic memory in induced pluripotent stem cells", vol. 467, No. 7313, 2010, pp. 285-290.
Kim et al., "Time-course transcriptional profiling of human amniotic fluid-derived stem cells using microarray" Cancer Res Treat, 2010, 42(2):82-94; whole document.
Kettle et al ("Mechanism of inactivation of myeloperoxidase by 4-aminobenzoic acid hydrazide," Biochem. J. (1997) 321, 503-508).
Kumano et al., "Generation of Induced pluripotent stem cells from primary chronic myelogenous leukemia patient samples", Blood vol. 119, No. 26, 2012, pp. 6234-6242.
Kuroda et al. "Treatment of A Full-Thickness Articular Cartilage Defect in the Femoral Condyle of an Athlete with Autologous Bone-Marrow Stromal Cells." Osteoarthritis and Cartilage, vol. 15, No. 2 (2007): 226-231.
Lee et al., "Xenogeneic human umbilical cord-derived mesenchymal stem cells reduce mortality in rats with acute respiratory distress syndrome compl icated by sepsis", Oncotarget, 2017, 8(28):45626-45642; whole document.
Lee et al., "Derivation of neural crest cells from human pluripotent stem cells". Nature protocols 5:88-701 (2010).
Lesage et al., "The amniotic fluid as a source of mesenchymal stem cells with lung-specific characteristics", Wiley Prenatal Diagnosis 2017, pp. 1093-1099.
Lindencrona et al., "CD4+ T Cell-Mediated Her-2/Neu-Specific Tunor Rejection In The Absence of B Cells"., Int J Cancer vol. 109, 2004, pp. 259-264.
Lith et al ("Engineering biodegradable polyester elastomers with antioxidant properties to attenuate oxidative stress in tissue," Biomaterials. Sep. 2014 ; 35(28): 8113-8122).
L. M. Reid, "Stem cell biology, hoemone/matrix synergies and liver differentiation". Current Opinion in Cell Biology, vol. 2, 1990, p. 121-130.
Leng et al., "Transplantation of ACE2-Mesenchymal stem Cells Improves the Outcome of Patients with COVID-19 Pneumonia", Aging Dis, Mar. 9, 2020, 11(2):216-228; whole document.
Marchetto et al., "Transcriptional Signature and Memory Retention of Human-Induced Pluripotent Stem Cells". Plos One vol. 4, No. 9, 2009, p. E7076.
Masip at al., "Reprogramming with defined factors: from induced pluripotency to induced transdifferentiation"., Molecular Human Reproduction, vol. 16, No. 11 pp. 856-868, 2010.
Melissa Ann Brown et al., "Umbilical Cord Blood Derived Endothelial Progenitor Cells: Isolation, Characterization, and Adhesion Potential in Vitro and in Vivo",, Jan. 1, 2009 (Jan. 1, 2009), XP055140385, Retrieved from the Internet: URL:http://hdl.handle.net/10161/1355 055140385 X.
Mareschi et al., "Multipotent Mesenchymal Stromal Stem Cell Expansion by Plating Whole Bone Marrow at a Low Cellular Density: A More Advantageous Method for Clinical Use", Stem Cells International, 2012, vol. 2012, pp. 1-10. (Year: 2010).
Maurice et al., "Isolation of progenitor cells from cord blood using adhesion matrices", Cytotechnology, 2007, vol. 54, pp. 121-133.
McGuckin et al., "Culture of embryonic-like stem cells from human umbilical cord blood and onward differentiation to neural cells in vitro," Nature Protocols, vol. 3, 2008, p. 1046-1055.
Mizuno et al., "Generation of skeletal muscle stem/progenitor cells from murine induced pluripotent stem cells," The Journal of the Federation of American Societies for Experimental Biology, vol. 24, 2010, p. 2245-2253.
Moraghebi et al., "Term amniotic fluid: an unexploited reserve of mesenchymalstromal cells for reprogramming and potential cell therapy applications" Stem Cell Res Ther, 2017,8(1):190; whole document.
Murphy et al., "Amnion Epithelial Cell Isolation and Characterization for Clinical Use," Current Protocols in Stem Cell Biology, vol. 13, 2010, p. 1-25.
M. V. Wiles, Embryonic Stem Cell Differentiation in vitro Meth. EnzymolL. vol. 225, 1993, p. 900.
Nijboer et al (Targeting the p53 Pathway to Protect the Neonatal Ischemic Brain, Ann Neural 2011; 70:255-264).
O'Donoghue et al., "Fetal stem cells," Best Practice & Research Clinical Obstetrics and Gynaecology, vol. 18, No. 6, pp. 853-875, 2004.
Osanai et al., "Enhanced expression of retinoic acid-metabolizing enzyme CYP26A1 in sunlight-damaged human skin"., vol. 44, No. 4, 2011, pp. 200-206.
Pak, "Regeneration of Human Bones in Hip Osteonecrosis and Human Cartilage in Knee Osteoarthritis With Autologous Adipose-Tissue-Derived Stem Cells: A Case Series." J Med Case Reports 5. 296 (2011).
Okabe et al., "Definitive proof for direct reprogramming of hematopoietic cells to pluripotency", Blood, 2009, vol. 114, No. 9, pp. 1764-1767.
Panopoulos et al., "Rapid and Highly Efficient Generation of Induced Pluripotent Stem Cells from Human Umbilical Vein Endothelial Cells", PLOS ONE, vol. 6, No. 5, May 16, 2011 (May 16, 2011), p. e19743, XP055035699, DOI: 10.1371/journal.pone.0019743 055035-699 X.
Park et al., "Disease-Specific Induced Pluripotent Stem Cells"., Cell vol. 134, No. 5, 2008, pp. 877-886.
Pereira et al., "Reproducible methodology for the isolation of mesenchymal stem cells from human umbilical cord and its potential for cardiomyocyte generation," Journal Of Tissue Engineering And Regenerative Medicine, vol. 2, 2008, p. 394-399.
Phuc et al., "Isolation of three important types of stem cells from the same samples of banked umbilical cord blood", Cell Tissue Bank, published online Jun. 8, 2011, vol. 13, pp. 341-351.
Polo et al., "Cell type of origin influences the molecular and functional properties of mouse induced pluripotent stem cells"., Nature Biotechnology, vol. 28, No. 8, 2010, pp. 848-855.
P.D. Rathjen et al., "Properies and uses of Embryonic Stem Cells Prospects for Application to Human Biology and Gene Therapy" Reprod. Fertil. Dev. vol. 10, 1998, p. 31.
Prigione et al ("The Senescence-Related Mitochondrial/Oxidative Stress Pathway is Repressed in Human Induced Pluripotent Stem Cells," Stem Cells 2010;28:721-733).
Ronn et al., Reactive Oxygen Species Impair the Function of CD90+ Hematopoietic Progenitors Generated from Human Pluripotent Stem Cells. Sep. 1, 2016, vol. 35, No. 1; pp. 197-206; p. 2, 1st column, 2nd paragraph to 2nd column, 2nd paragraph; p. 3, 1st column, 1st and 2nd paragraphs; plage 4, 2nd column, 2nd paragraph; DOI: 10.1002/slem.2503.
Ronn et al., "Retinoic Acid Regulates Hematopoietic Development from Human Pluripotent Development from Human Pluripotent Stem Cells", Stem Cell Reports, vol. 4, No. 2, Feb. 1, 2015, pp. 269-281, XP055333217, United States ISSN: 2213-6711, DOI: 10.1016/j.stemcr.2015.01.009, p. 271, col. 1, paragraph 2.
Robertson, "Teratocarcinomas and embryonic stem cells: A practical approach", 1987, IRL Press Ltd.
Roubelakis, M.G., et al., "In vitro and in vivo properties of distinct populations of amniotic fluid mesenchymal progenitor cells," Journal of Cellular and Molecular Medicine, vol. 15, 2011, p. 1896-1913.
Saguil et al., "Acute Respiratory Distress Syndrome: Diagnosis and Management", American Family Physician, 2012, vol. 85, No. 4, pp. 352-358, 2012.
Spitzhorn et al., "Isolation and Molecular Characterization of Amniotic Fluid-Derived Mesenchymal Stem Cells Obtained from Caesarean Sections", Hindawi Stem Cells International, vol. 2017, Article ID 5932706, in 15 pages.

(56) References Cited

OTHER PUBLICATIONS

Salehinejad et al., "Comparison of different methods for the isolation of mesenchymal stem cells from human umbilical cord Wharton's jelly," In Vitro Cell.Dev.Biol.—Animal (2012) 48:75-83.
Saxena et al., "Cyclic AMP Signaling through Epac Axis Modulates Human Hemogenic Endothelium and Enhances Hematopoietic Cell Generation", Stem Cell Reports, vol. 6, No. 5, May 1, 2016, pp. 692-703, XP055333169, United States ISSN: 2213-6711, DOI: 10.1016/j.stemcr.2016.03.006 p. 695, col. 1, paragraph 2; figure 1.
Savickiene et al., "Human Amniotic Fluid Mesenchymal Stem Cells from Second- and Third-Trimester Amniocentesis: Differentiation Potential, Molecular Signature, and Proteome Analysis," Stem Cells International, 2015, in 15 pages.
Schiavo, A.A., et al., "Endothelial properties of third-trimester amniotic fluid stem cells cultured in hypoxia," Stem Cell Research & Therapy, (2015) 6:209, p. 1-15.
Seshareddy et al. "Method to Isolate Mesenchymal-Like Cells from Wharton's Jelly of Umbilical Cord," Methods in Cell Biology, vol. 86, 2008, p. 101-119.
Takahashi et al., "Induction of Pluripotent Stem Cells from Mouse Embryonic and Adult Fibroblast Cultures by Defined Factors"., Cell vol. 126, No. 4, 2006, pp. 663-676.
Vadasz et al., "Second and third trimester amniotic fluid mesenchymal stem cells can repopulate a de-cellularized lung scaffold and express lung markers," Journal of Pediatric Surgery, 2014, in 10 pages.
Vega, et al., 2017. "High-Content Image Informatics of The Structural Nuclear Protein Numa Parses Trajectories for Stem/Progenitor Cell Lineages and Oncogenic Transformation". Exp. Cell Res. 351:11-23.
Vizcardo et al. "Regeneration of Human Tumor Anitigen-Specific T Cells from iPSCs Devrived from Mature CD8 T Cells", Cell Stem Cell, Jan. 3, 2013, vol. 12, No. 1, pp. 31-36.
Wang et al ("Calpain inhibitor attenuates ER stress-induced apoptosis in injured spinal cord after bone mesenchymal stem cells X transplantation," Neurochemistry International 97: 15-25 (Jul. 2016).
Wassarman et al., "Guide to Techniques in Mouse Development", Methods in Enzymology vol. 225, 1993.
Weiss et al., "Stem Cells in the Umbilical Cord," Stem Cell Review, vol. 2, 2006, p. 155-162.
Wisniewski et al. (Further phenotypic characterization of the primitive lineage-CD34+CD38−CD90+CD45Ra-hematopoietic stem cell/progenitor cell sub-population isolated from cord blood, mobilized peripheral blood and patients with chronic myelogenous leukemia. Blood Cancer Journal. 2011).
You, Q., et al., "Isolation of human mesenchymal stem cells from third-trimester amniotic fluid," International Journal of Gynecology and Obstetrics, vol. 103, 2008, p. 149-152.
Ye et al., "Human-induced pluripotent stem cells from blood cells of healthy donors and patients with acquired blood disorders"., Blood vol. 114, No. 27, 2009, pp. 5473-5480.
Yu et al., "Induced Pluripotent Stem Cell Lines Derived from Human Somatic Cells"., Science vol. 318, No. 5858, 2007, pp. 1917-1920.
Zhou et al., "Amniotic fluid-derived mesenchymal stem cells: characteristics and therapeutic applications" Arch Gynecol Obstet, 2014, 290(2):223-231; whole document.
Zhou et al., "Generation of human induced pluripotent stem cells from urine samples," Nature Protocols, vol. 7, 2012, p. 2080-2089.
Flow Rate Units Conversion, Traditional Oven, 5 pages, retrieved from the internet (May 0, 2022): https://www.traditionaloven.com/tutorials/flow-rate/convert-gtt-drop-per-minute-to-ml-milliliter-per-hour.html (Year: 2022).
Hong, D.K., et al., "Combined treatment with Dichloroacetic acid and pyruvate reduces hippocampal neuronal death after transient cerebral ischemia," Frontiers in Neurology, Mar. 2018, vol. 9, Article 137 (in 11 pages).
Iizuka, H., et al., "Targeted gene correction of RUNX1 in induced pluripotent stem cells derived from familial platelet disorder with propensity to myeloid malignancy restores normal megakaryopoiesis," Experimental Hematology, 2015, vol. 43, pp. 849-857.
Kinney, M.A., et al., "A systems biology pipeline identifies regulatory networks for stem cell engineering," Nature Biotechnology, 2019, vol. 37, pp. 810-818.
Li, Yaqing, et al., "Therapeutic effects of amniotic fluid-derived mesenchymal stromal cells on lung injury in rats with emphysema," Respiratory Research (2014) 15:120.
Ma, Q-S., et al., "Ligand-based design, synthesis and biological evaluation of xanthine derivatives as LSD1/KDM1A inhibitors," European Journal of Medicinal Chemistry, 2018, vol. 162, pp. 555-567 (Accepted Manuscript).
Naik, P.O., et al., "Mitophagy-driven metabolic switch reprograms stem cell fate," Cellular and Molecular Life Sciences, Sep. 28, 2018, vol. 76, pp. 27-43.
Oburoglu, L., et al., "Glucose and Glutamine Metabolism Regulate Human Hematopoietic Stem Cell Lineage Specification," Cell Stem Cell, 2014, vol. 15, pp. 169-184.
Pelus, L.M., et al., "Peripheral Blood Stem Cell Mobilization: a Look Ahead," Current Stem Cell Reports, 2018, vol. 4, pp. 273-281.
Shigemura, T., et al., "Mosaicism of an ELANE mutation in an asymptomatic mother," Journal of Clinical Immunology, Jan. 2019, vol. 39, pp. 106-111.
Suzuki, H., et al., "Glycolytic pathway affects differentiation of human monocytes to regulatory macrophages," Immunology Letters 176: 18-27 (2016), Accepted Manuscript.
Uchida, N., et al., "Efficient generation of □-globin-expressing erythroid cells using stromal cell-derived induced pluripotent stem cells from patients with sickle cell disease," Stem Cells, 2017, vol. 33, pp. 586-596.
Vodyanik, M.A., et al., "Leukosialin (CD53) defines hematopoietic progenitors in human embryonic stem cell differentiation cultures," Blood, 2006, vol. 108, pp. 2095-2105.
Wilson, Jennifer G., et al., "Mesenchymal Stem (Stromal) Cells for Treatment of ARDS: A Phase 1 Clinical Trial", Lancet Respir Med. Jan. 2015; 3(1): 24-32.
International Search Report in PCT/SE2020/051139 dated Jan. 28, 2021.

\* cited by examiner

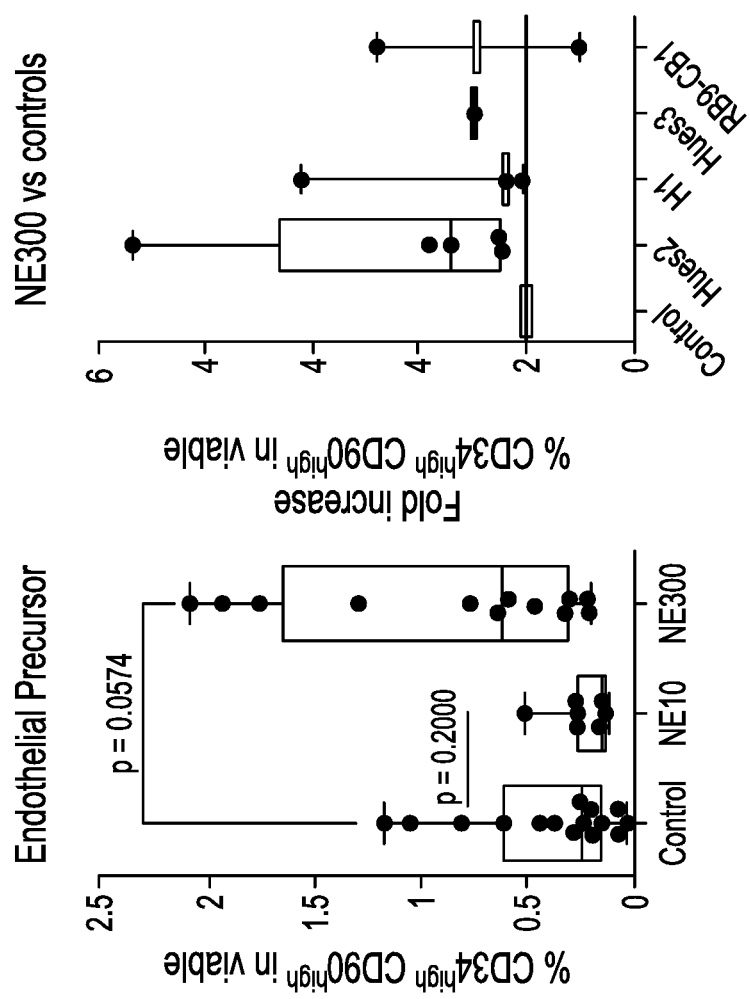
FIG. 2K
FIG. 2J
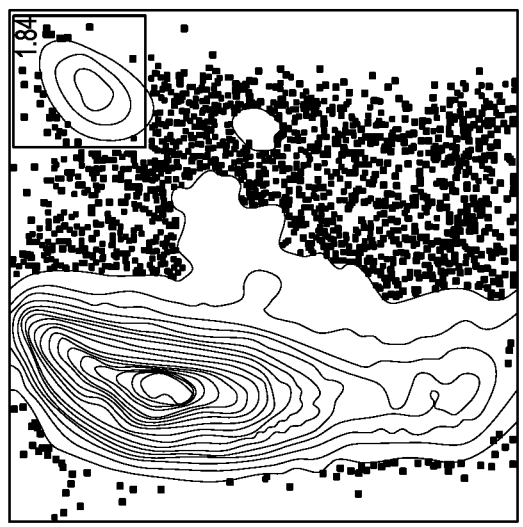
FIG. 2I

SEQUENCE LISTING

```
<160> NUMBER OF SEQ ID NOS: 20

<210> SEQ ID NO 1
<211> LENGTH: 22
<212> TYPE: DNA
<213> ORGANISM: Artificial Sequence
<220> FEATURE:
<223> OTHER INFORMATION: PCR primer

<400> SEQUENCE: 1
tgacaatgag gtttcttcgg ct                                              22

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
gactgggctc tcgatgtgac                                                 20

<210> SEQ ID NO 3
<211> LENGTH: 21
<212> TYPE: DNA
<213> ORGANISM: Artificial Sequence
<220> FEATURE:
<223> OTHER INFORMATION: PCR primer

<400> SEQUENCE: 3
gctccggttt tggggtatct g                                               21

<210> SEQ ID NO 4
<211> LENGTH: 20
<212> TYPE: DNA
<213> ORGANISM: Artificial Sequence
<220> FEATURE:
<223> OTHER INFORMATION: PCR primer

<400> SEQUENCE: 4
gcgttgatgt gaggttccag                                                 20

<210> SEQ ID NO 5
<211> LENGTH: 21
<212> TYPE: DNA
<213> ORGANISM: Artificial Sequence
<220> FEATURE:
<223> OTHER INFORMATION: PCR primer
```

```
<400> SEQUENCE: 5
ggtgggccaa aggatgaaga g                                        21

<210> SEQ ID NO 6
<211> LENGTH: 20
<212> TYPE: DNA
<213> ORGANISM: Artificial Sequence
<220> FEATURE:
<223> OTHER INFORMATION: PCR primer

<400> SEQUENCE: 6
ccacaagcca aacgacttcc                                          20

<210> SEQ ID NO 7
<211> LENGTH: 23
<212> TYPE: DNA
<213> ORGANISM: Artificial Sequence
<220> FEATURE:
<223> OTHER INFORMATION: PCR primer

<400> SEQUENCE: 7
ggtagatttc aatacgttcc ggg                                      23

<210> SEQ ID NO 8
<211> LENGTH: 23
<212> TYPE: DNA
<213> ORGANISM: Artificial Sequence
<220> FEATURE:
<223> OTHER INFORMATION: PCR primer

<400> SEQUENCE: 8
tgacagttct cctgatgtcc aaa                                      23

<210> SEQ ID NO 9
<211> LENGTH: 21
<212> TYPE: DNA
<213> ORGANISM: Artificial Sequence
<220> FEATURE:
<223> OTHER INFORMATION: PCR primer

<400> SEQUENCE: 9
tgttgctgga gaatcgggtt c                                        21

<210> SEQ ID NO 10
<211> LENGTH: 23
<212> TYPE: DNA
<213> ORGANISM: Artificial Sequence
<220> FEATURE:
<223> OTHER INFORMATION: PCR primer

<400> SEQUENCE: 10
tcccagttac catcttctgt gta                                      23

<210> SEQ ID NO 11
<211> LENGTH: 23
<212> TYPE: DNA
<213> ORGANISM: Artificial Sequence
<220> FEATURE:
<223> OTHER INFORMATION: PCR primer

<400> SEQUENCE: 11
ttccagaata ccaacgtcaa agg                                      23

<210> SEQ ID NO 12
```

```
<211> LENGTH: 21
<212> TYPE: DNA
<213> ORGANISM: Artificial Sequence
<220> FEATURE:
<223> OTHER INFORMATION: PCR primer

<400> SEQUENCE: 12
gttttcggcc agcagctatt g                                           21

<210> SEQ ID NO 13
<211> LENGTH: 22
<212> TYPE: DNA
<213> ORGANISM: Artificial Sequence
<220> FEATURE:
<223> OTHER INFORMATION: PCR primer

<400> SEQUENCE: 13
gcttcagcag attatgcgtc tg                                          22

<210> SEQ ID NO 14
<211> LENGTH: 21
<212> TYPE: DNA
<213> ORGANISM: Artificial Sequence
<220> FEATURE:
<223> OTHER INFORMATION: PCR primer

<400> SEQUENCE: 14
gtttcttgcc tcatggcttg g                                           21

<210> SEQ ID NO 15
<211> LENGTH: 19
<212> TYPE: DNA
<213> ORGANISM: Artificial Sequence
<220> FEATURE:
<223> OTHER INFORMATION: PCR primer

<400> SEQUENCE: 15
aagctgagcc gacccttttc                                             19

<210> SEQ ID NO 16
<211> LENGTH: 21
<212> TYPE: DNA
<213> ORGANISM: Artificial Sequence
<220> FEATURE:
<223> OTHER INFORMATION: PCR primer

<400> SEQUENCE: 16
ccaatgacgt tctcatgctg c                                           21

<210> SEQ ID NO 17
<211> LENGTH: 21
<212> TYPE: DNA
<213> ORGANISM: Artificial Sequence
<220> FEATURE:
<223> OTHER INFORMATION: PCR primer

<400> SEQUENCE: 17
acatgagaag ctaggcgagg a                                           21

<210> SEQ ID NO 18
<211> LENGTH: 21
<212> TYPE: DNA
<213> ORGANISM: Artificial Sequence
<220> FEATURE:
<223> OTHER INFORMATION: PCR primer

<400> SEQUENCE: 18
```

```
ggcagcgtgg atatacctca g                                        21

<210> SEQ ID NO 19
<211> LENGTH: 16
<212> TYPE: DNA
<213> ORGANISM: Artificial Sequence
<220> FEATURE:
<223> OTHER INFORMATION: PCR primer

<400> SEQUENCE: 19
ccccgcgagc acagag                                              16

<210> SEQ ID NO 20
<211> LENGTH: 20
<212> TYPE: DNA
<213> ORGANISM: Artificial Sequence
<220> FEATURE:
<223> OTHER INFORMATION: PCR primer

<400> SEQUENCE: 20
atcatccatg gtgagctggc                                          20
```

METHODS AND COMPOSITIONS FOR GENERATING HEMATOPOIETIC CELLS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

REFERENCE TO SEQUENCE LISTING, TABLE, OR COMPUTER PROGRAM LISTING

The present application is being filed along with a Sequence Listing in electronic format. The Sequence Listing is provided as a 7 kb file entitled EVHO001.004WO.TXT, created on Oct. 19, 2016, providing in electronic format subject matter which was present in the disclosure as originally filed. The information in the electronic format of the Sequence Listing is incorporated herein by reference in its entirety.

STATEMENT REGARDING PRIOR DISCLOSURE BY THE INVENTOR OR A JOINT INVENTOR

Part of the present invention was disclosed by the inventors in Saxena et al., "Cyclic AMP Signaling through Epac Axis Modulated Human Hemogenic Endothelium and Enhances Hematopoietic Cell Generation," *Stem Cell Reports* 6(5):692-703 (10 May 2016, online date 21 Apr. 2016).

FIELD OF THE INVENTION

The present disclosure relates generally to methods of inducing and controlling the generation of blood from pluripotent stem cells or reprogrammed cells via activation of cyclic adenosine monophosphate (cAMP) and may include activation of the Exchange proteins activated by cAMP (Epac) axis utilizing cAMP and/or Epac activators. Cells produced by this method show a greater propensity to develop as hematopoietic precursors and hematopoietic cells, where the hematopoietic cells possess features indicative of superior function for use in transplantation for the treatment of hematologic disorders or malignancies.

BACKGROUND

Hematopoietic stem cells (HSC) replenish hematopoiesis throughout the lifetime of an individual and can be transplanted into patients to treat malignant and non-malignant blood disorders. However, there is often a lack of qualified or willing donors, and some conditions require autologous transplants. Therefore, significant numbers of patients (estimated 20-30% patients) who require a bone marrow transplant cannot receive the life-saving treatment because they do not have access to sufficient numbers of HLA-matched HSCs. Even more patients would benefit from having a more suitably matched donor to reduce the unwanted effects of graft vs. host disease. Additional patients where an alternative source of HSCs would be beneficial are: where contaminating malignant cells or premalignant cells from traditional HSC sources (e.g. bone marrow) are present, or where there is an inability to mobilize autologous HSCs due to the disease itself (e.g. multiple myeloma) or following secondary and tertiary chemotherapy regimens (i.e. relapsed patients where the stored stocks of autologous HSCs have already been transplanted). Depending on the source of somatic cells for deriving the iPS cells, or for deriving blood cells from direct reprogramming protocols, these pluripotent or reprogrammed cell derived HSCs and blood cells may in fact be superior to traditionally harvested HSCs and blood cells in terms of: 1) reduced acquired mutations (e.g. if iPS cells were derived from neonatal cell sources), 2) unlimited expansion ability, 3) reduced rejection issues, 4) no contaminating cells from the original tumor present, and 5) the ability to genetically correct mutated genes in cells from patients using existing technologies such as Talens, zinc-finger endonucleases, or the more recent CRISPR/Cas DNA recombination system. Moreover, recent advances in the ability to generate T-cells specifically designed to target and destroy malignant cells following their differentiation from pluripotent and reprogrammed cells (See Lindencrona et al. Int J Cancer 2004, Vizcardo et al. Cell Stem Cell 2013), means that transplantations could be performed with simultaneous HSC and anti-tumor T-cells. As such, the ability to generate new blood and new blood stem cells would be able to serve an immediate demand for donor cells for many patients, and potentially offers an exponential increase in use as the surrounding technologies advance. Some blood cells generated using in vitro protocols may be able to be form without going through an HSC stage, depending on numerous factors including whether newly generated blood cells have gone through developmental stages of maturation to an adult HSC such as coming from precursors of the hematopoietic system that do not generate HSCs but do generate blood cells. Further differentiation of HSCs may also support the development of mature cells such as erythrocytes or erythroid cells for transplantation, and for the production of artificial blood products, which could greatly relieve the burden placed on the blood donation system, in which donor shortages frequently lead to shortages in the blood supply. Accordingly, there is a need to develop an alternative source of HSCs and other blood cells with features and properties similar to adult donors, where there is a high degree of matching of the HLA types. HSCs, blood cells generated from pluripotent stem cells, or blood cells generated from reprogrammed somatic cells (whether the cells are reprogrammed directly into hematopoietic cells, or reprogrammed into precursors of the hematopoietic system, such a endothelial cells with hemogenic potential) are examples of cells that would meet this need.

Methods for isolating cells, cell reprogramming, generating pluripotent and multipotent cells, and tissue, organ, and stem cell therapies, are needed for a variety of therapeutic applications, including personalized and regenerative medicine. A variety of human stem cells and other cell types are known, including embryonic stem cells, isolated during early embryonic development, and somatic stem cells such as mesenchymal or adult stem cells. Somatic cells can be reprogrammed into more primitive stages of similar or related developmental lineages, or into pluripotent stem cells, or alternatively they may be reprogrammed into altogether different cell lineages which then may be able to differentiate into multiple types of cells of that lineage. For example in the formation of blood cells, fibroblasts have been reprogrammed into erythrocyte progenitors and endothelial cells have been reprogrammed into hemogenic endothelial cells.

For example, human umbilical cord blood from newborn infants has been used as a source of hematopoietic stem cells for transplantation to patients with hematological disorders and malignancies for decades, due to the high proportion of blood stem cells present in the material. In another example, cells may be isolated from amniotic fluid. The in vitro generation of hematopoietic stem and progenitor cells by differentiation of pluripotent stem cells (embryonic stem cells and induced pluripotent stem cells) or from cells reprogrammed directly into blood related lineages such as mesoderm, endothelium, or blood cells directly, requires controlled conditions that regulate numerous factors. For example, BMP4 (Bone morphogenetic protein 4) is required to stimulate efficient mesodermal tissue differentiation from pluripotent stem cells. Another example is that retinoic acid signaling is required in the development of hematopoietic stem cells as they emerge. While other factors have been identified, there are likely numerous additional factors which have not yet been identified that play a role in generating blood. Moreover, the de novo generation of blood in vivo and the generation of blood in vitro will also likely differ as developmental programs cannot yet be exactly mirrored in vitro. However, in vitro systems that direct generation of blood may allow for greater control and thereby greater frequency and efficiency of blood cell generation.

For the blood cells to be suitable for transplantation and long-term engraftment, generated HSCs must be capable of homing, self-renewal, proliferation and differentiation into all lineages of the hematopoietic system including erythrocytes. Molecular signals received during the development of the hematopoietic system are required in order for HSCs to possess these features. Present methods of generating de novo blood cells in vitro do not adequately provide these signals, and thus do not yield sufficient numbers of cells nor cells with the required characteristics. The present disclosure provides novel methods of generating HSCs and blood cells that address the some of the shortcomings of the presently available methods.

Molecular signaling in cells involved in the development of blood, including upstream signaling in a precursor to blood, such as endothelial cells or actual blood cells, is important for the survival, maturation, and proliferation of stem cells ultimately leading to functional hematopoietic cells. It has also been suggested that signaling in development may provide maturation signals or epigenetic marks that allows for specific functional as the cells reach their adult stage. Norepinephrine signaling has recently been shown to be required during murine embryonic development to produce repopulating HSCs. However its role in human development and more importantly in the development of blood from in vitro based systems such as pluripotent stem cell differentiation, or direct reprogramming of cells towards blood or blood precursors was previously unknown.

Several studies have recently reported important functions of the peripheral nervous system (PNS) for hematopoiesis, in HSC function as well as in HSC specification during embryonic development. Direct interaction of the PNS with HSCs has also been suggested given the expression of the β2-adrenergic receptor (ADRB2) on HSCs, reported in human cord-blood CD34+CD38− cells, as well as on the nascent HSCs in murine AGM. In addition, this receptor is up-regulated in mobilized HSCs and upon in vitro exposure to G-CSF and GM-CSF, suggesting an important role of adrenergic signaling for HSC egress from the bone marrow (BM). Indeed, administration of epinephrine to mice increased HSC egress from the BM. The same article also reported that exposure of cord-blood CD34+CD38− cells to catecholamines enhanced their motility in vitro as well as their ability to repopulate NOD-SCID mice.

Likewise, regarding the adult BM niche and HSC mobilization, it has been shown that synchronization of HSC egress from the BM with the circadian rhythm is mediated by norepinephrine-secreting via sympathetic fibers in the bone marrow. The relevance of the adult bone marrow PNS components for HSC function has been suggested to be related to the role of adrenergic innervation in BM hematopoietic recovery following genotoxic insults, as well as by the evidence of TGF-β signaling regulation by neural crest-derived non-myelinating Schwann cells, essential for bone marrow HSC maintenance.

During development, the evaluation of the interaction between the developing PNS and HSC emergence has been limited. However, in the murine AGM it has been suggested that there is an interaction in which the spatio-temporal correlation of neural crest migration and maturation in the vicinity of the dorsal aorta (DA) coincides with emergence of the first HSCs. These Neural Crest structures contain the precursors for the peripheral nervous system and are gradually established next to the mouse DA, from days E8.5 to E14.5. They further mature and express tyrosine hydroxylase (TH), the rate-limiting enzyme for catecholamine production, from day E10.5 onwards, coinciding developmentally with the emergence of the first hematopoietic cells from the ventral side of the DA.

It has been suggested that there could be a connection between the developing PNS and the emergence of the first HSCs in the DA, that neural crest-derived cells could provide signals to the DA, triggering hematopoietic cell emergence and conceivably promoting their maturation into functional HSCs. This hypothesis was recently confirmed in a Gata3−/− mouse study, where secretion of catecholamines by the developing PNS was indeed demonstrated to be essential for the emergence and function of the first HSCs, likely through ADRB2 signaling.

Accumulating evidence suggests that hematopoietic development originates from endothelial-to-hematopoietic transition (EHT). Single cell transcriptional analyses of murine cells in a blood development contexts shows cells comprising of both endothelial and hematopoietic lineages, with a continuum of cells having endothelial to hematopoietic signatures. These cells include precursors of HSCs, hemogenic endothelium, as well as other precursors of the blood lineage, and newly emergent blood cells and committed blood cells. The newly identified EHT subpopulations which are precursors to blood cells are an interesting cell type for further discovery as the hematopoietic lineages potentials—the types of blood cells capable of being generated by the differing precursors—are likely already predefined. Thus the EHT, conversion to blood, of precursor cells or reprogrammed cells requires specific signals to be able to generate blood cells with specific features.

SUMMARY OF THE INVENTION

The present disclosure is directed to methods and media for the production of precursor cells of the hematopoietic lineage, hematopoietic cells (HSCs), and to the cells produced thereby. It will be understood by one of skill in the art that the cells described herein are not limited to a specific type of cell unless otherwise specified, but are cells related to blood in that they are either precursors of the blood lineage, or will be able to generate blood using methods of converting cells from other lineages, or are newly derived blood cells from non blood cells. ie. the cells are precursors to blood that developmentally upstream of committed blood which may include mesodermal, or endothelial cells. These may be derived from pluripotent stem cells. Such cells may also include non-blood cells that are not typically considered related to blood such as a fibroblasts, where through reprogramming by what ever means, the cell is converted to a cell related to blood, such as, for example a mesodermal, endothelial or blood cell itself. There may also be some cells that following reprogramming or following specific culturing that may also be more related to particular blood lineages or precursors of blood, which are included as blood related (e.g. an endothelial cell that may be converted through reprogramming to hemogenic endothelium). Cells related to blood may also include the de novo generated blood from a non-blood cell (eg but not limited to endothelial cell) in an in vitro culture system.

In embodiments, a method of producing hematopoietic cells via activation of the cAMP-Epac axis, comprises:

(a) obtaining cells that are capable of differentiating or converting into hematopoietic cells;

(b) culturing said cells under conditions that specify them towards the hematopoietic lineage; and (c) culturing the said cells in a medium that comprises an activator of the cyclic adenosine monophosphate (cAMP), and/or the cAMP Exchange proteins activated by cAMP (Epac) signaling axis, thereby obtaining hematopoietic cells.

In some embodiments, the relevant precursor cell may be, or originate from, one or more of a pluripotent stem cell, human pluripotent stem cell (hPSC), human embryonic stem cell (hESC), a reprogrammed somatic cell, such as but not limited to an induced pluripotent stem cell (iPSC) or a cell reprogrammed toward an endothelial lineage, a hemogenic endothelial cell (hematopoietic stem cell arising from an endothelial lineage), or any combination thereof. In some further embodiments, the relevant cAMP activator may be one or more of forskolin, IBMX, norepinephrine, epinephrine, salmeterol, isoproterenol, N6,O2-dibutyrl-adenosine-3',5'-cyclic monophosphate (db-cAMP) and 8-bromo-adenosine-3',5'-cyclic monophosphate (8-Br-cAMP), Bucladesine, 6-Bnz-cAMP, cAMPS-Sp, triethylammonium salt, N6-Monobutyryladenosine 3':5'-cyclic monophosphate sodium salt, 8-Bromoadenosine 3',5'-cyclic monophosphate, Adenosine 3',5'-cyclic monophosphate, CW008 (4-Fluoro-N-[5-fluoro-6-(5-methoxypyrazolo[1,5-a]pyridin-3-yl)-1H-pyrazolo[3,4-b]pyridin-3-yl]benzamide), Cholera toxin, Prostaglandins, or any combination thereof. In some embodiments, the cells are expanded prior to differentiation, either at step (a) or (b), as above. In some embodiments, the precursor cell, cAMP-Epac activator, and/or incubation conditions are selected such that inhibition of Epac is reduced or avoided. Activation of the Epac axis may be cAMP-dependent or may be independent of cAMP activation. In some embodiments, the cAMP activation leads to the upregulation of the homing factor protein CXCR4 on the surface of the cells. In some embodiments the cAMP activation leads to the reduction of intracellular ROS levels in the cells and their progeny and may also provide reduced DNA damage, protein damage, and/or lipid damage in said cells. In some embodiments, reduction of ROS in adult derived hematopoietic stem cell cultures produces cells with increased repopulating activity. In some embodiments, oxidative stress is minimized via one or more of: control of environmental oxygen levels; application of redox state modifiers; or any combination thereof. In some further embodiments, the methods as described herein provide for selective enhancement of erythroid cell production, with concomitant reduction in the number of macrophages produced. In some embodiments, selective removal of macrophages during the differentiation process is contemplated. In some embodiments, the methods as described above provide a means for producing hematopoietic stem cells, erythroid cells, erythrocytes, B-cells T-cells NK-cells or other hematopoietic cells. In some embodiments, said cells may be used for transplantation to treat hematologic disease or malignancy, or may be used to provide an artificial blood product for transfusion.

DETAILED DESCRIPTION

Figure 1B:
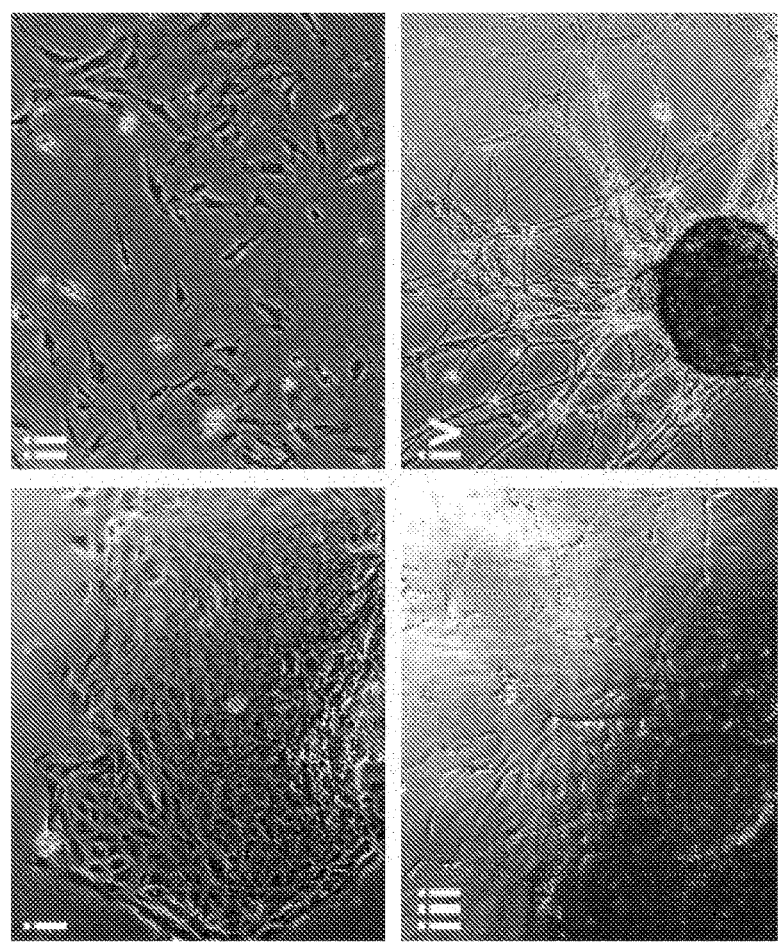
FIG. 1. A) Scheme of a transversal section of the AGM region of a human fetus. AGM—aorta-gonad-mesonephros; DA—dorsal aorta; UG—Urogenital Ridges; B) Representative micrographs of cellular growth following culture of AGM explants dissected from human fetuses: i: outgrowth with endothelial morphology; ii: outgrowth of stromal morphology; iii: outgrowth with neurosphere morphology from the DA region of the 42 days-old fetus; iv: outgrowth with neurosphere morphology from the DA region of the 58 days-old fetus. i and ii were taken from explants of the UG region of the 58 days-old fetus; C) Fluorescence microscopy pictures of the neurosphere-like structures stained for MAP2 and GFAP; D) Time-line of hPS-to-blood induction experiment, with neural-crest-conditioned media added for the last 4 days of the protocol (from time of emergence to endpoint) E) Gating strategy for the FACS analysis at the endpoint of the hES-to-blood differentiation protocol; F) Fold increase in percentage of the different hematopoietic subsets outlined in E, conditioned media versus control settings (n=1).
Figure 1A:
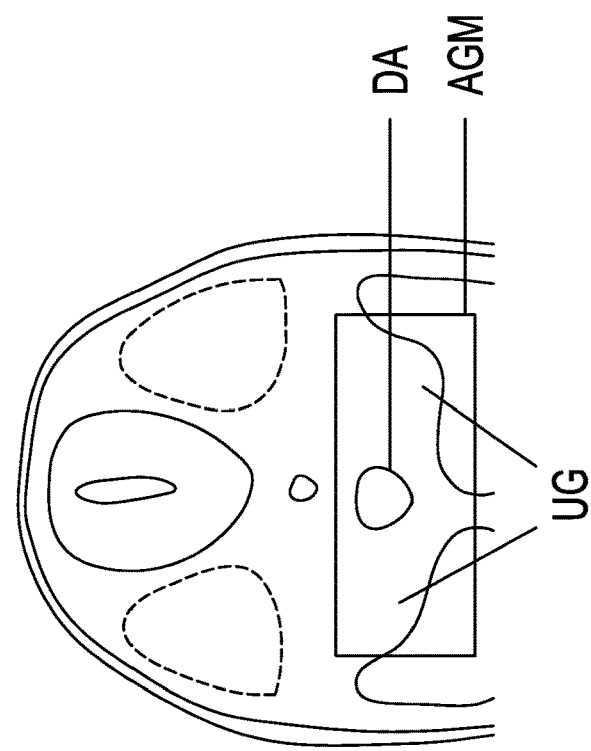
Figure 1C:
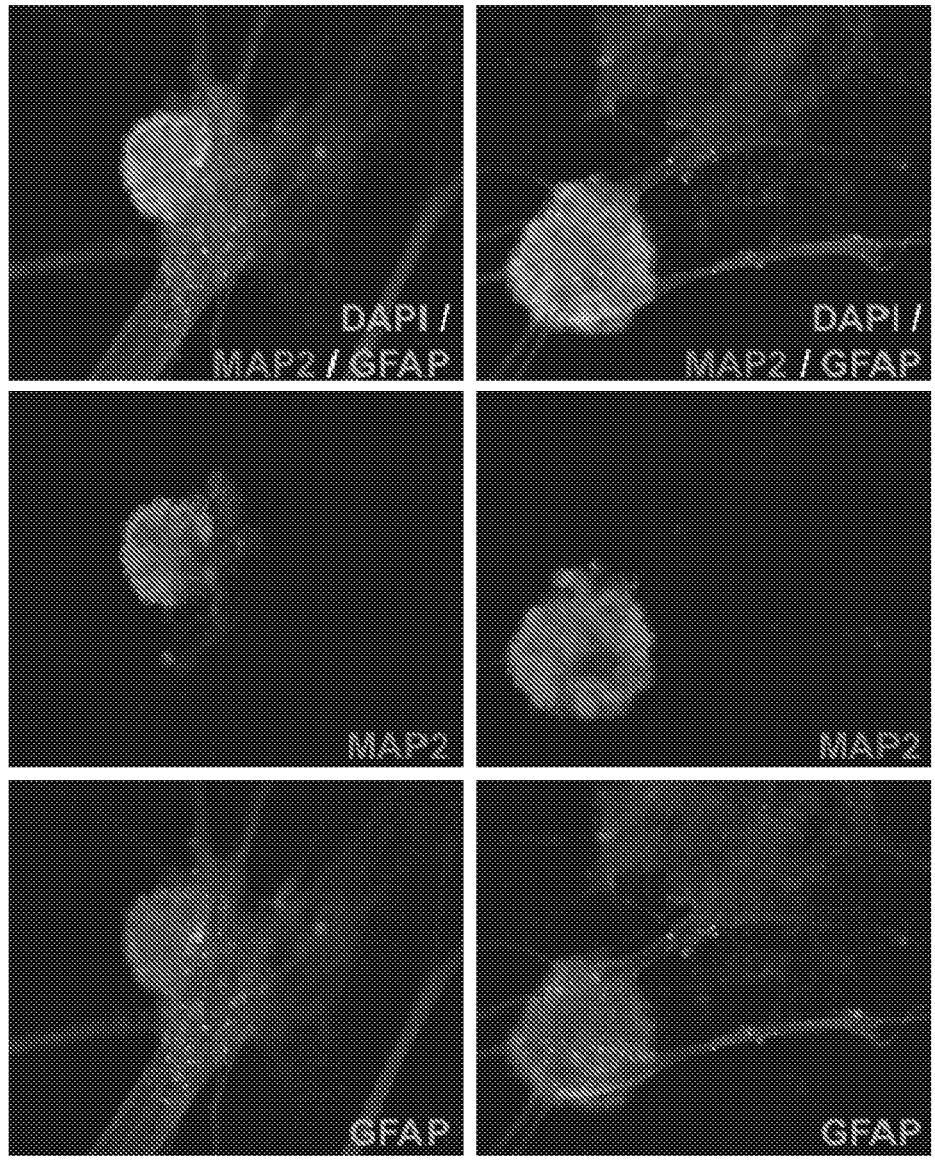

Activation of specific G-protein coupled receptors by catecholamines, as well as neurotransmitters, growth factors and hormones activates the cyclic AMP (cAMP) signaling pathway, and is followed by cell-type dependent responses mediated by cAMP effectors Protein Kinase A (PKA) and Exchange proteins activated by cAMP (Epac). Epac have been shown to modulate endothelial cell remodeling, enhances endothelial cell adhesion, and regulates the integrity of endothelial cell junctions, however, the role of Epac in the endothelial-to-hematopoietic transition (EHT) was previously unknown. While norepinephrine signaling is clearly involved in hematopoietic stem cell function, the mechanism of catecholamine signaling, through its second messenger, cyclic AMP (3'-5'-cyclic adenosine mono phosphate), and its downstream signaling pathways had not previously been evaluated in the context of hematopoietic development. Moreover, the importance of cAMP in in vitro systems for the generation of de novo blood e.g., pluripotent stem cell differentiation, and the direct preprogramming of somatic cells to hematopoietic cells or hematopoietic precursors had previously not been demonstrated.

Cyclic AMP-mediated regulation of adult hematopoiesis has been suggested in studies showing that: cAMP increases C—X—C chemokine receptor type 4 (CXCR4) expression and motility of hematopoietic progenitors, HSCs from Gsα-deficient mice do not engraft, and Gsα-deficient osteocytes alter the BM niche, leading to defective hematopoiesis. In human hematopoietic cells, Prostaglandin E2 (PGE2)-mediated cAMP activation enhances human cord blood engraftment. Recently, cAMP has been shown to regulate hematopoietic emergence and homing in studies where cAMP was upregulated by adenosine in zebrafish and mouse, by PGE2 in zebrafish and mouse, and by shear stress in murine AGM. However, the role and mechanism of cAMP signaling, as mediated through PKA and Epac, in regulating human developmental hematopoiesis had not been adequately studied, and no study had previously been performed on the role of cAMP in the human hematopoietic developmental context.

Human pluripotent stem cells (hPSC), including human embryonic stem cells (hESC) and induced pluripotent stem cells (iPSC), can be used in the in vitro generation of de novo blood for therapeutic purposes. We have shown that hPSC-derived HSC-like cells possess lymphoid and myeloid differentiation ability, a key feature of HSCs. Recent studies have functionally demonstrated an endothelial precursor to blood (hemogenic endothelium) from hPSC differentiation cultures, further establishing hPSCs as a suitable model to study human hematopoietic cell development. However, the signals regulating EHT in human hematopoiesis remain undefined. Additionally, for functional transplantable HSCs, it is vital to reduce reactive oxygen species (ROS) and oxidative stress, as reduced ROS is crucial for HSC functionality.

As cAMP-mediated regulation of human hematopoietic cell emergence previously had remained elusive, we set out to investigate the role of cAMP signaling in hPSC-derived hematopoietic emergence. We have found that in the in vitro generation of de novo blood from pluripotent stem cells, cAMP induction increases the frequency of cells with HSC-like surface phenotype and increases the colony-forming potential. Furthermore, we have discovered that cAMP regulation of human HSC-like cell emergence is dependent on the cAMP-Epac signaling axis, where endothelial cells which may contain the endothelial precursors of a hematopoietic lineage require exogenous signaling. We disclose that this cAMP-mediated increase in HSC-like cells is in part coupled to cAMP-mediated mitigation of oxidative burden and increasing hematopoietic cell function.

Unless otherwise specified, all terms used in disclosing the invention, including technical and scientific terms, have the meaning as commonly understood by one of ordinary skill in the art to which this invention belongs. By means of further guidance, term definitions may be included to better appreciate the teaching of the present invention.

As used herein, "progenitor cell" means a cell from a human or from any other animal that can be induced by the methods described herein to differentiate into a hematopoietic cell. Such cells include but are not limited to: pluripotent stem cells, human pluripotent stem cells (hPSC), human embryonic stem cells (hESC), induced pluripotent stem cells (iPSC), hemogenic endothelial cells, or reprogrammed somatic cells, into hematopoietic cells (HCs). In some instances, the progenitor cell may be a precursor endothelial cell or a hemogenic endothelial cell. Such cells may also be isolated from amniotic fluid or umbilical cord blood.

As used herein, "hematopoietic cell" means a cell differentiated for function in the blood. Such cells include, but are not limited to granulocytes, macrophages, and erythroid cells including erythrocytes.

As used herein, "isolated," when used to describe a cell or cells, refers to a cell or cells that have been separated from their natural environment, including by separation from the subject from which the cell is derived, e.g., a patient, and/or by separation from one or more other components of the natural environment, such as debris, tissue, tissue aggregates, and other cells.

As used herein, "fetal" is used to describe the property of a cell or other material derived from a developing mammal, such as a human, after the embryonic stage and before birth.

As used herein, "pluripotent" refers to the ability of a cell to differentiate into cell types of any of the three germ layers, endoderm, mesoderm, and ectoderm. "Multipotent" refers to the ability of a cell to differentiate into cells of a number of multiple, but a limited number of lineages.

The phrase "stem cell(s)" may be used throughout the specification. It will be understood by one of skill in the art that "stem cell(s)" may refer to adult stem cells or embryonic stem cells and human or animal stem cells. For example, such stem cells may include induced pluripotent stem (iPS) cells that have been generated from multiple adult cell types, including skin, fibroblasts and other cells and tissues. A variety of stem cells are currently used therapeutically or evaluated for use in clinical trials, including somatic cells, such as mesenchymal stem cells, and hematopoietic stem cells, e.g., for use in neurological and hematological disorders, respectively.

The phrase "reprogrammed somatic cell" may be used throughout the specification. It will be understood by one of skill in the art that "reprogrammed somatic cell" is not limited to a particular type of somatic cell, but rather may refer to any type of somatic cell. Takahashi and Yamanaka first described reprogramming technologies to "reprogram" or "de-differentiate" somatic cells into a pluripotent/embryonic like state, or to directly "reprogram" somatic cells into another cell lineage type. Takahashi and Yamanaka, 2006, Cell 126(4): 663-676. For example, reprogrammed somatic cells may refer to reprogrammed cells from epithelial, connective, nervous, muscle tissues and/or from blood, such as umbilical cord blood. For example, cord blood derived endothelial progenitor cells and adipose-derived stem cells are suitable for reprogramming. A reprogrammed somatic cell may also refer to a cell that is directly induced to becoming another cell type entirely, e.g. a fibroblast directly into an endothelial cell or alternatively into a hematopoietic cell.

As used herein, "differentiation" means the process of conversion of a progenitor cell into a mature cell, differentiated cell, such as a hematocyte or other hematopoietic cell. "differentiation" may also refer to the time during which such maturation occurs.

As used herein, "cAMP-Epac axis" refers to the signaling pathway incorporating cyclic adenosine monophosphate (cAMP) and Exchange proteins activated by cAMP (Epac). The cAMP-Epac axis comprises cAMP, various adenylyl cyclase enzymes, as well as various Epac proteins and their downstream targets, the Ras family GTPases Rap1 and Rap2. Epac proteins comprise a group of 3',5' cyclic adenosine monophosphate (cAMP)-regulated guanine nucleotide exchange factors including Epac1, also referred to as cAMP-GEFI, and Epac2, also referred to as cAMP-GEFII. Epac proteins activate the Ras family GTPases Rap1 and Rap2 by promoting GTP binding in a cAMP-dependent manner. "Activation" of the cAMP-Epac axis refers to signaling events that occur via this signaling pathway as would occur in the presence of cAMP. It is contemplated that, according to the embodiments disclosed herein, activation of Epac proteins may occur in the absence of cAMP or may be effected by activators other than cAMP.

In the following description of certain embodiments provided here, reference is made to the accompanying drawings which form a part hereof, and in which it is shown by way of illustration specific embodiments in which the invention can be practiced. It is to be understood that other embodiments can be used and structural changes can be made without departing from the scope of the invention.

The methods described herein provide for the enhanced differentiation of progenitor cells, such as pluripotent stem cells, human pluripotent stem cells (hPSC), human embryonic stem cells (hESC), induced pluripotent stem cells (iPSC), hemogenic epithelial cells, or reprogrammed somatic cells, into hematopoietic cells (HCs). As described herein, said methods provide an application of the discovery that activation of the cAMP-Epac axis provides more complete and more efficient maturation of pluripotent stem cells and reprogrammed somatic cells into HCs. As described herein, HCs having undergone cAMP-Epac mediated differentiation or maturation have enhanced survival, enhanced transplantability, and greater utility in the treatment of hematologic disorders or malignancies, or in the development of artificial blood products for transfusion.

One of ordinary skill in the art will be able to obtain pluripotent stem cells, human pluripotent stem cells (hPSC), human embryonic stem cells (hESC), induced pluripotent stem cells (iPSC), hemogenic epithelial cells, reprogrammed somatic cells, or the like by the application of such conventional methods as are well known in the art for the isolation or production of such cells.

In some embodiments, the methods of the present disclosure comprise culturing stem cells under conditions that direct mesodermal development. Such conditions may include the generation of embryoid bodies, which may be achieved, for example, by culturing cells in a medium containing MesoTotal™ HPC/HSC Differentiation System (Primorigen Biosciences, Madison, Wis., USA) or other equivalent growth media. Mesodermal differentiation may also be directed by the addition of growth factors such as Granulocyte-Macrophage Colony Stimulating Factor (GM-CSF), Interleukin-3 (IL-3), Interleukin-6 (IL-6), Granulocyte Colony Stimulating Factor (G-CSF), Stem Cell Factor (SCF), Erythropoietin (EPO), and combinations thereof.

Embryoid body formation is one mechanism of generating blood precursors, but is not a necessary step to generate blood from pluripotent stem cells (PSCs). Direct differentiation is also possible where the EB production step is bypassed and the PSCs are directly differentiated into blood with suitable growth factors and conditions that allow for blood production, as previously described. cAMP induction during this direct differentiation process will likely have similar effect on the production and features of the blood cells as the developmental stages of differentiation from the pluripotent stem cells (primarily the endothelial cells transitioning to hematopoietic cells) will be similar to EB mediated generation of blood.

Given the multiple methods of artificially generating de novo blood from non-blood cells (such as through direct reprogramming), in some embodiments the methods described herein provide desired features to the newly generated blood cells from these additional non-blood cell sources where blood cells are the desired outcome. According to the methods as described herein, endothelial cells can be directly reprogrammed to generate hemogenic endothelial cells that are capable of producing HSCs and other blood cell types. Similarly fibroblast can directly reprogrammed to convert to erythroid progenitors and other blood cells. In both these case, the starting cells are considered non-blood cells and go through a conversion towards hematopoietic lineage commitment. In both these cases, the culture of these cells in the presence of activators of cAMP will also generate hematopoietic cells with the additional features that cAMP or cAMP-EPAC activation provides, i.e. CXCR4 upregulation, reduction of ROS, improvement in cell numbers and or frequencies of hematopoietic cells including hematopoietic stem cells and progenitors. According to an embodiment of the methods and cells as described herein, these cells with cAMP activation will thus better mirror features of adults hematopoietic cells in terms of their function, and phenotypes as described herein. Other examples of direct reprogramming have demonstrated generation of blood cells and thus the desired cAMP directed alterations of the features of blood cells can be applied to these methods as well.

The methods described herein may utilize signaling through the β2-adrenergic receptor (ADRB2) pathway. However, we note that ADRB2-independent pathways are more likely to be utilized in the cAMP-mediated induction of hematopoiesis.

In some embodiments, the methods as described herein provide for the administration of an activator of the cAMP-Epac axis to a selected cell population. In some embodiments, the selected population comprises pluripotent stem cells or reprogrammed somatic cells. In some embodiments, the administration comprises addition of the activator to the growth medium that is applied to the cells. In some other embodiments, the administration comprises the addition of the activator to the growth matrix. In some embodiments, the activator increases cAMP by activating adenylyl cyclase. In some embodiments, the activator comprises a phosphodiesterase inhibitor. In some embodiments, the activator comprises one or more of catecholamines, as well as neurotransmitters, growth factors and hormones or any combination thereof. In some embodiments, the activator comprises one or more of norepinephrine, epinephrine, forskolin, IBMX, Prostaglandin E2 (PGE2), or any combination thereof, or other compounds known in the art to activate the cAMP-Epac axis. In some embodiments, a growth medium with an elevated level of adenosine, adenosine monophosphate (AMP), cyclic adenosine monophosphate (cAMP), adenosine diphosphate (ADP), or adenosine triphosphate (ATP) may be provided. In some further embodiments, the methods as described herein provide for a method of enhancing the efficiency or degree of maturation of HCs, wherein Epac inhibition is minimized.

In some embodiments, the cAMP activator is added at a concentration as is known in the art to provide for activation of the cAMP-Epac axis. In some embodiments, the final concentration of the activator within the cell growth medium is 5 mM. In some embodiments, the final concentration of the activator within the cell growth medium is 10 mM. In some embodiments, the final concentration of the activator within the cell growth medium is 20 mM. In some embodiments, the final concentration of the activator within the cell growth medium is 30 mM. In some embodiments, the final concentration of the activator within the cell growth medium is 40 mM. In some embodiments, the final concentration of the activator within the cell growth medium is 50 mM. In some embodiments, the final concentration of the activator within the cell growth medium is 100 mM. In some embodiments, the final concentration of the activator within the cell growth medium is 150 mM. In some embodiments, the final concentration of the activator within the cell growth medium is 200 mM. In some embodiments, the final concentration of the activator within the cell growth medium is 250 mM. In some embodiments, the final concentration of the activator within the cell growth medium is 300 mM.

In some embodiments, the Epac axis is activated via direct activation of Epac proteins. Such activation may be achieved using commercially available Epac activators, such as, for example, 8-(4-Chlorophenylthio)-2'-O-methyladenosine 3',5'-cyclic Monophosphate, (S)-Adenosine, cyclic 3',5'-(hydrogenphosphorothioate); (S)(P)-8-Bromo-Adenosine 3',5'-cyclic Monophosphorothioate; and (S)(P)-Adenosine 3',5'-cyclic monophosphorothioate.

To provide for the maturation of HCs from pluripotent stem cells or reprogrammed somatic cells, an activator of the cAMP-Epac axis should be provided at a time during the maturation process in which such activation would be maximally advantageous. In some embodiments, the methods provided herein include the administration of a cAMP-Epac activator on day 8 after the initiation of HC differentiation. In some embodiments, administration of said cAMP-Epac activator is made on day 9 after the initiation of HC differentiation. In some embodiments, administration of said cAMP-Epac activator is made on day 10, 11, 12, 13, or 14 after the initiation of HC differentiation. In some embodiments, administration of a cAMP-Epac activator occurs on multiple occasions during the maturation protocol. In some embodiments, a first administration occurs on day 8, 9, 10, 11, 12, 13, or 14 of the maturation protocol. In some further embodiments, a second administration occurs one, two, three, four, or more days after the first administration. In some further embodiments, a third, fourth, fifth, or further administration is made. In some embodiments, the cAMP-Epac activator is infused continuously into the growth medium. In some further embodiments, the cAMP-Epac activator is applied continuously over the course of 1, 2, 3, 4, 5 or more days.

To provide for the maturation of HCs from pluripotent stem cells or reprogrammed somatic cells, said cells and cultures thereof should not be exposed to inhibitors of Epac during the differentiation process. Such inhibitors include but are not limited to: α-[(2-(3-Chlorophenyl)hydrazinylidene]-5-(1,1-dimethylethyl)-β-oxo-3-isoxazolepropanenitrile (ESI-09); 8-(4-chlorophenylthio)-2'-O-methyladenosine-3',5'-cyclic monophosphate; 8-(4-Chlorophenylthio)-2'-O-methyladenosine-3',5'-cyclic monophosphate, acetoxymethyl ester; Brefeldin A, 4-Methylphenyl-2, 4, 6-trimethylphenylsulfone (ESI-05); and 4-cyclopentyl-2-[[(2,5-dimethylphenyl)methyl]thio]-1,6-dihydro-6-oxo-5-pyrimidinecarbonitrile (HJC0197).

In some embodiments, the methods described herein provide for the reduction in the presence of immune cells during differentiation. It has been found by the inventors that the presence of macrophages and granulocytes during maturation of hematopoietic cells is disadvantageous for the production of erythroid cells. Therefore, according to the methods described herein, cAMP activation is carried out such that differentiation into erythroid cells is enhanced while differentiation into macrophages is not enhanced, or is suppressed. Selective removal of macrophages during the maturation process is also contemplated. Suppression or selective removal of macrophages may be achieved using compounds known in the art to effect the selective inhibition of macrophage development. One such compound is imatinib.

Hematopoietic cells emerge from hemogenic endothelium in the developing embryo through the endothelial-to-hematopoietic transition (EHT). However, many mechanisms behind human hematopoietic development remain unclear. We have found that cyclic adenosine mono phosphate (cAMP) upregulates HSC-like cells and increases CFU potential. We have also shown that the cAMP Exchange proteins activated by cAMP (cAMP-Epac) axis regulates human hematopoietic cell emergence; Epac inhibition decreases the hemogenic endothelium and subsequently decreases blood/HSC generation. We have additionally discovered that cAMP-mediated hematopoietic cell upregulation is in part due to mitigated oxidative stress, creating a redox-state balance, and enhancing C—X—C chemokine receptor type 4 (CXCR4) expression. Collectively, our studies have provided new insights and mechanistic details regarding the previously unrecognized role of cAMP signaling in regulating human hematopoietic development. These findings have advanced the mechanistic understanding of hematopoietic development, allowing us to develop transplantable human hematopoietic cells for therapeutic needs.

In some embodiments, therefore, the methods described herein provide for the control of reactive oxygen species or free radicals within the growth chamber, within the growth medium, within any scaffolding or support, or in the area surrounding the differentiating cells. It has been found by the inventors that reduction in ROS or free radicals leads to increases in the fraction of erythroid cells, as well as increased robustness and longevity of such cells, leading to superior transplantability as compared to cells differentiated in the presence of ROS. Therefore, in some embodiments according to the methods described herein, the cells are incubated in the presence of ROS scavengers or antioxidants. Exemplary scavengers, antioxidants, or redox modifiers include but are not limited to: ascorbic acid, citric acid, vitamin E, selenium, melatonin, NAC, glutathione, thioredoxin, nicotinamide adenine dinucleotide phosphate, Superoxide dismutase, Catalase, and Glutathione peroxidase. In some embodiments, control of ambient environmental conditions, including the mixture of gases present in the growth chamber, is utilized to minimize the formation of ROS or free radicals. In some embodiments, minimization of the presence of macrophages as described above assists in, or achieves, a reduction in ROS or free radicals. In some embodiments, C—X—C chemokine receptor type 4 (CXCR4) expression is enhanced.

Further, the present disclosure relates to cells that are produced by the methods disclosed herein. Said cells may be erythroid cells which may be transplanted in order to treat, prevent, or ameliorate a hematologic disorder or malignancy. Such disorders may include anemias, thalassemias, sickle cell disease, or infectious diseases such as malaria, babesiosis, chagas disease, leishmaniasis, or similar conditions. In some embodiments, said cells may be used to produce an artificial blood product for transfusion.

The methods and cells described herein are further illustrated by the following examples.

Example 1

In murine development, the generation of definitive hematopoietic stem cells with lympho-myeloid adult repopulating ability occurs at day 10.5 post coitum (E10.5). These cells, capable of adult hematopoiesis, first appear in the aorta-gonad-mesonephros (AGM) region of the embryo proper, suggesting that signals from the AGM region enable de novo generation, survival and maturation of transplantable Hematopoietic Stem Cells (HSCs). In contrast, the hematopoietic progenitors emerging from the yolk sac (YS) at earlier time point during development are not capable of lympho-myeloid reconstitution of adult recipients. In the human embryo, a similar pattern of development has been suggested, with the YS giving rise initially to primitive lineage-restricted hematopoietic cells, while later the cells emerging in the major vessels of the Splanchnopleura/AGM region are endowed with definitive hematopoietic potential. In the AGM, specifically, the first HSCs have been shown to emerge from the endothelium lining the ventral side of the dorsal aorta (DA). This process of emergence of the HSCs from an endothelial precursor has been coined endothelial-to-hematopoietic transition (EHT).

Several studies have recently reported important functions of the peripheral nervous system (PNS) for hematopoiesis, in HSC function as well as in HSC specification during development. Direct interaction of the PNS with HSCs has also been suggested given the expression of the β2-adrenergic receptor (ADRB2) on HSCs, reported in human cord-blood CD34+CD38− cells, as well as on the nascent HSCs in murine AGM). In addition, this receptor is up-regulated in mobilized HSCs and upon in vitro exposure to G-CSF and GM-CSF, suggesting an important role of adrenergic signaling for HSC egress from the bone marrow (BM). Indeed, administration of epinephrine to mice increased HSC egress from the BM. The same article also reported that exposure of cord-blood CD34+CD38− cells to catecholamines enhanced their motility in vitro as well as their ability to repopulate NOD-SCID mice.

Likewise, regarding the adult BM niche and HSC mobilization, it has been shown that synchronization of HSC egress from the BM with the circadian rhythm is mediated by norepinephrine-secreting via sympathetic fibers in the bone marrow. The relevance of the adult bone marrow PNS components for HSC function was further revealed by the importance of adrenergic innervation for BM hematopoietic recovery following genotoxic insults, as well as by the evidence of TGF-β signaling regulation by neural crest-derived non-myelinating Schwann cells, essential for bone marrow HSC maintenance.

During development, the evaluation of the interaction between the developing PNS and HSC emergence has been limited. However, in the murine AGM the spatio-temporal correlation of neural crest migration and maturation in the vicinity of the dorsal aorta (DA) may coincide with emergence of the first HSCs. These Neural Crest structures contain the precursors for the peripheral nervous system and are gradually established next to the mouse DA, from E8.5 to E14.5. They further mature and express tyrosine hydroxylase (TH), the rate-limiting enzyme for catecholamine production, E10.5 onwards, coinciding developmentally with the emergence of the first hematopoietic cells from the ventral side of the DA.

It has also been suggested that there could be a connection between the developing PNS and the emergence of the first HSCs in the DA, that neural crest-derived cells could provide signals to the DA, triggering hematopoietic cell emergence and conceivably promoting their maturation into functional HSCs. Secretion of catecholamines by the developing PNS has been demonstrated to be essential for the emergence and function of the first HSCs, likely through ADRB2 signaling.

Here we report that the addition of PNS neurotransmitter Norepinephrine (NE) to differentiating human ES/iPS cells significantly increases the frequency of the most immature HSC-like progenitors, as well as of the developmental endothelial precursor of definitive hematopoiesis. Modulation of this signaling by addition of a specific ADRB2 antagonist showed that this effect is unlikely to be mediated through this receptor, contrarily to what has been suggested during murine development.

Material and Methods

Pluripotent Stem Cell Culture and Hematopoietic Differentiation:

Human ES (H1, Hues3 and Hues2) and iPS (RB9-CB1) cell lines were expanded and differentiated towards the hematopoietic lineage as described in Rom et al., Stem Cell Reports 4:269-281. (2015). After EB plating at day 8 of differentiation, the adrenergic stimulating/inhibiting compounds (Norepinephrine at 10 μM and 300 μM from Sigma, ICI118,551 at 20 μM from Tocris) were added at day 10 and 12, before the final analysis at day 14.

Neural Crest Induction and NC-Conditioned Media

The differentiation of hPS cell lines towards Neural Crest Stem Cells was performed as published in Lee et al., Nature protocols 5:88-701 (2010). Specifically, hPS cell lines were transferred to a matrigel-mTeSR (Stem Cell Technologies)-based expansion system, after reaching confluency they were singularized with Accutase and plated on matrigel-coated 6-well plates at a cell density of 10×104 to 15×104 cells per well. For the first 48 h, mTeSR medium was supplemented with Rock-inhibitor. mTeSR media was changed daily until the cultures reached approximately 50% confluency. The media was then switched to KSR media (KO-DMEM with 15% KO-Serum, 1% Glutamax, 1% non-essential aminoacids, 55 μM beta-mercaptoethanol) supplemented with Noggin (500 ng/ml, R&D Systems) and SB431542 (10 μM, Tocris). The cultures were maintained for 11 days, with a progressive change from KSR to N2 medium (DMEM-F12 with 1×N2 supplement (Invitrogen), 3.1 g/L Glucose, 2 g/L NaHCO$_3$). At the end of the protocol cells were harvested with Accutase treatment and re-plated on Poly-L-ornithine-Laminin-Fibronectin-coated (concentration?) 6-well plates at the density of 50×104 cells/well. The percentage of neural crest stem cells in the cultures was assessed by flow-cytometry as p75+ HNK1+(supplemental data?). Hematopoiesis-inducing media Mesototal (Primorigen Biosciences, Madison, Wis., USA) was added to the neural-crest cells overnight, centrifuged to remove debris and transferred on the blood differentiation media.

Colony Forming Unit Assay

CFU potential of hematopoietic cells after the 14 day differentiation assay was assessed by plating 2×104 cells in Methocult H4230 (Stem Cell Technologies) supplemented with human SCF (25 ng/ml), GM-CSF (50 ng/ml), IL3 (25 ng/ml) and Erythropoietin (5 U/ml). Cells were incubated in a humidified incubator at 37° C., 5% CO2 for 14 days and colonies were quantified by bright-field microscopy.

FACS Analysis

The cells were collected after brief Trypsin treatment and flow cytometry was carried out as described in Rönn et al. (2015). The antibodies used were: CD43-FITC (BD Biosciences), CD45-FITC (BD Biosciences), CD34-PECy7 (Biolegend), CD38-APC (Biolegend), CD90-PE (Biolegend), CD45RA-V450 (BD Biosciences). Neural crest stem cells were assessed with flow cytometry using p75 and HNK1 antibodies (company?) for staining. 7-aminoactinomycin D (7AAD) was added to the samples prior to the analysis for excluding dead cells.

Results

Neural Crest Stem Cell-Conditioned Media Increases the Frequency of HSC-Like Cells Derived from iPSCs.

Figure 1D:
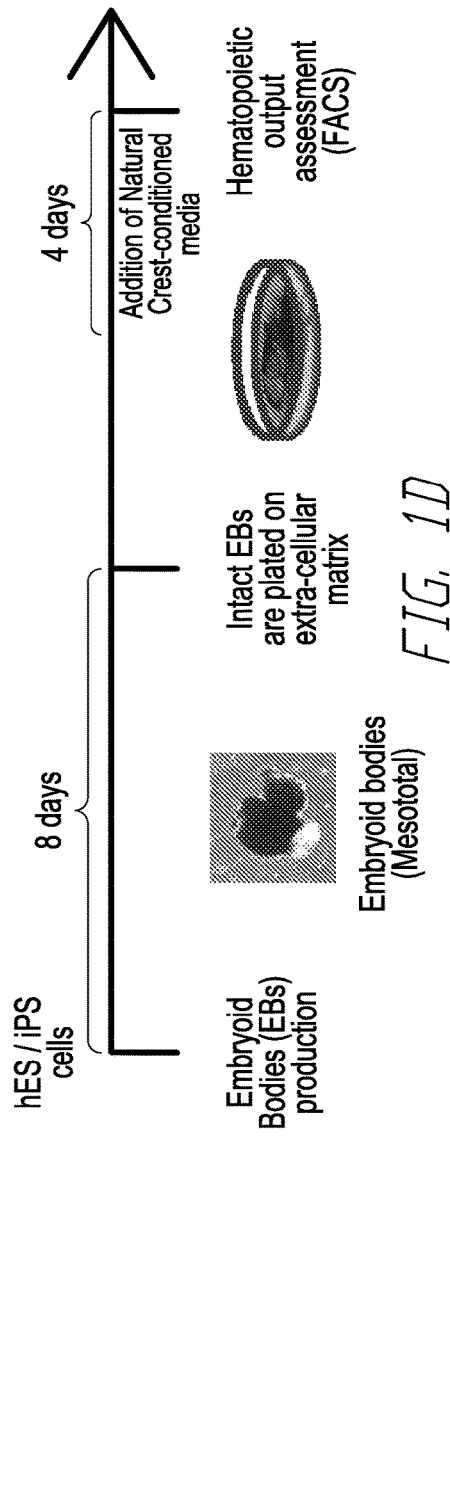
Figure 1F:
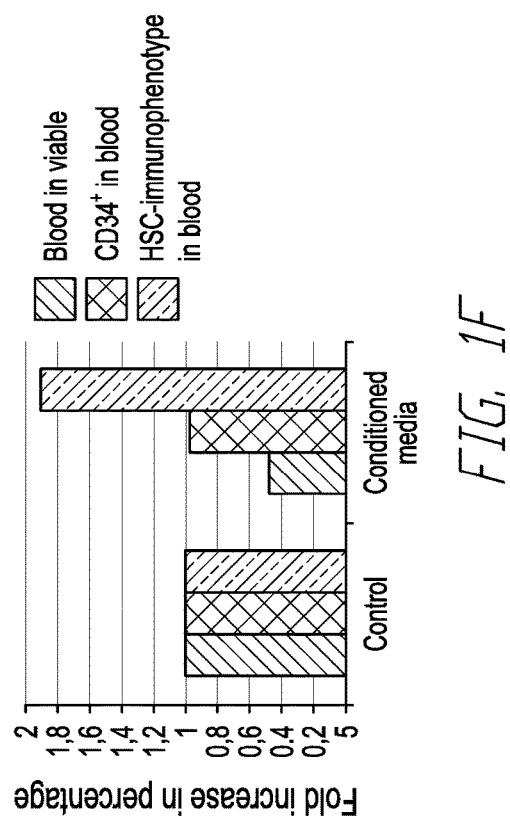
Figure 1E:
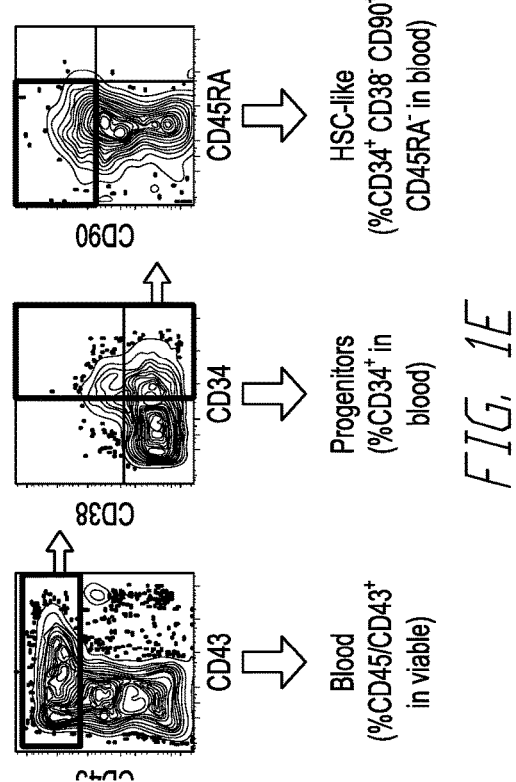

In order to assess whether neural crest-derived signals could benefit iPS-derived-hematopoietic cells, we used an established protocol to first generate neural crest cells and applied the neural crest-conditioned media on differentiating iPS cells. The conditioned media was applied from day 10 of the differentiation protocol, at the time when hematopoietic emergence can be detected, see FIG. 1D. Hematopoietic cells were then assessed by measuring the frequency of whole blood (CD43/45+), CD34+ progenitors within blood, and HSC-like cells (CD43/45+CD34+CD38−CD90+ CD45RA−), see FIG. 1E. We have previously shown that the latter population harbors cells with lymphoid and myeloid differentiation ability and displays surface makers that are known to be present on engrafting HSCs in the AGM. The addition of neural crest-conditioned media yielded a 2-fold increase in the frequency of HSC-like cells, see FIG. 1F.

Addition of Norepinephrine at the Time of Hematopoietic Emergence Increases Frequencies of HSC Phenotype, CFU Potential, and Endothelial Precursors.

Figure 2A:
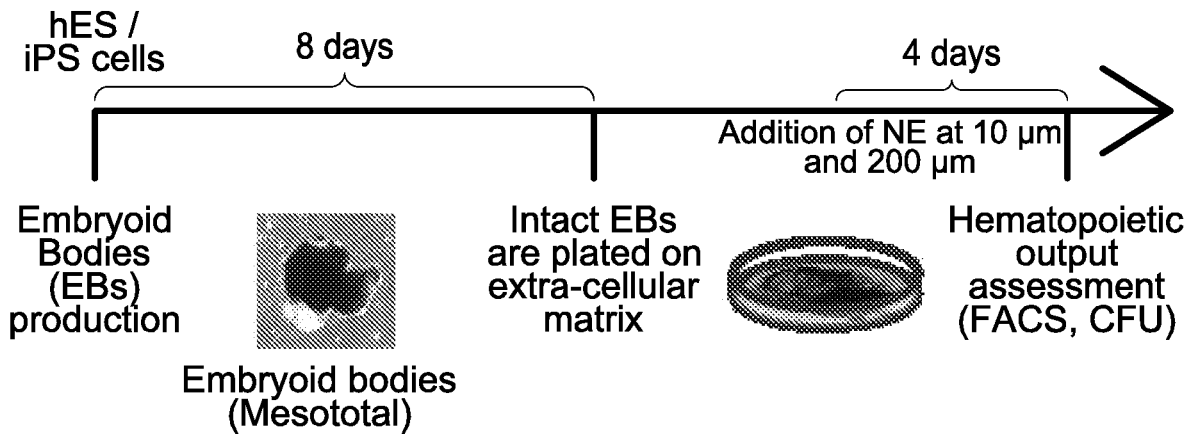
FIG. 2. Norepinephrine added to hPS-to-blood at the time of emergence increases frequencies of HSC phenotype, CFU potential, and endothelial percursors. A) Time-line of the hPS-to-blood differentiation experiment, with Norepinephrine added at two different concentrations for the last 4 days of the protocol (from time of emergence to endpoint); B) Box and whisker plot of the percentage of cells, in the total viable population, with an HSC-like immunophenotype (n=7 to 12); C) Box and whisker plot of the fold difference (NE300 vs controls) of the HSC-like immunophenotype in the total viable population showing separately the different human ES (Hues2, Hues3, H1) and iPS (RB9-CB1) cell lines used in the experiments; D) Box and whisker plot of the percentage of CD43/45+ hematopoietic cells in the total viable population (n=7 to 12); E) Box and whisker plot of the percentage of CD34+ cells in the total CD43/45+ blood population (n=7 to 12) F) Box and whisker plot of the percentage of CD34+CD38+CD90+CD45RA− cells in the total CD43/45+ blood population (n=7 to 12); G) Box and whisker plot of the CFU counts per 20 000 plated cells in methylcellulose. (n=8); H) Bar graph of the average colony type distributions registered in the experiments shown in G. Error bars correspond to standard deviation (n=8); I) Gating strategy for assessing the frequency of CD34high CD90high endothelial precursor of definitive hematopoiesis in the total viable population; J) Box and whisker plot of the percentage of CD34high CD90high endothelial precursor in the total viable population (n=7 to 12); K) Box and whisker plot of the fold difference (NE300 vs controls) of the CD34-high CD90-high endothelial precursors in the total viable population showing separately the different human ES and iPS cell lines used in the experiments. Each data-point represents an independent experiment. * p<0.05  p<0.01; * p<0.001; p values calculated with two-tailed paired Student t-tests
Figure 2B:
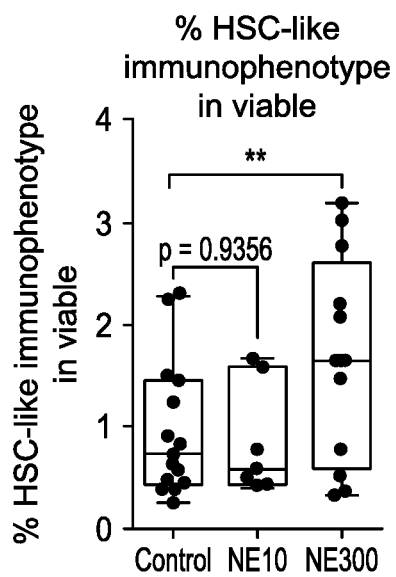
Figure 2C:
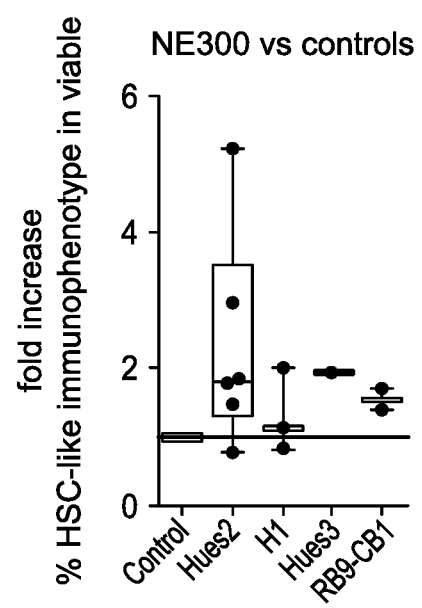
Figure 2F:
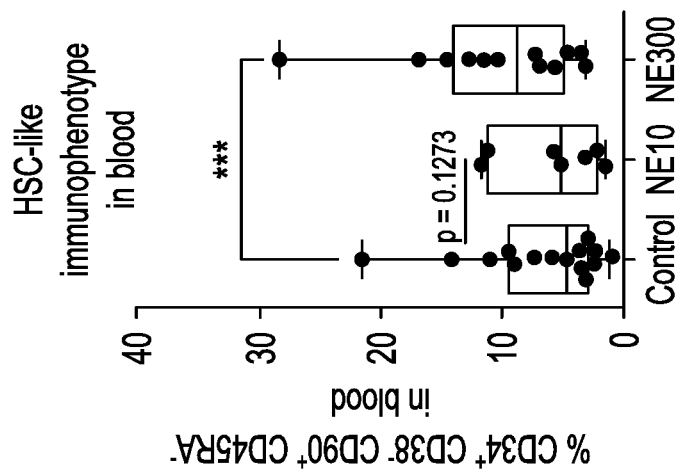
Figure 2E:
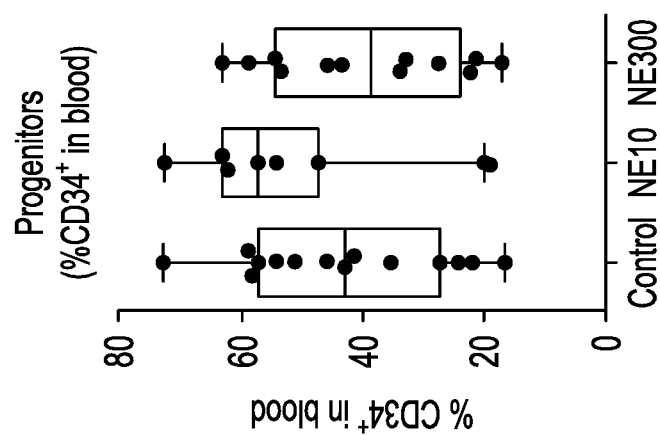
Figure 2D:
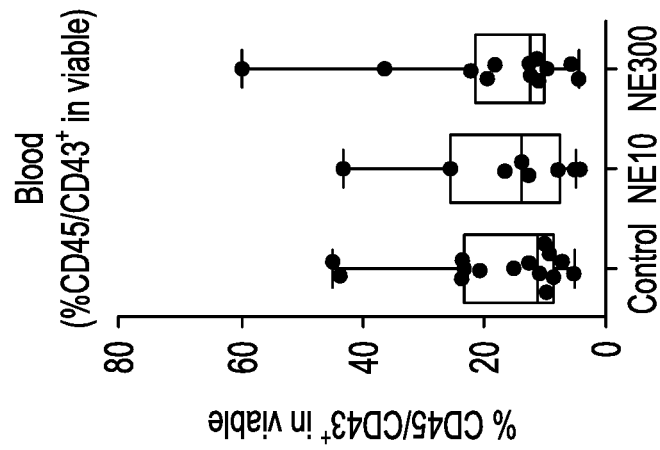
Figure 2H:
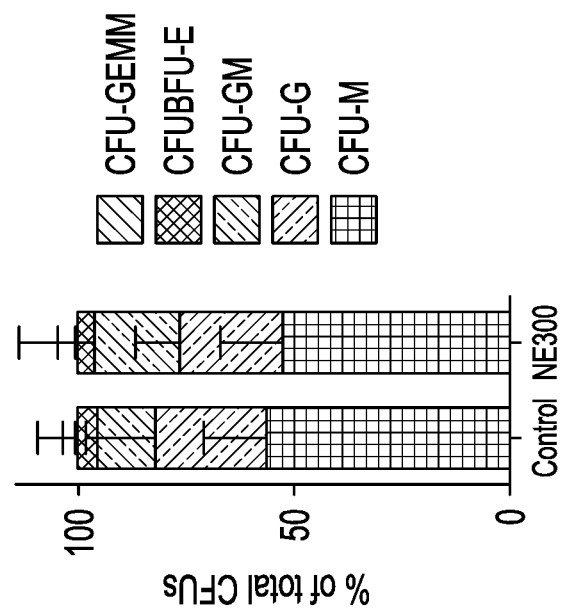
Figure 2G:
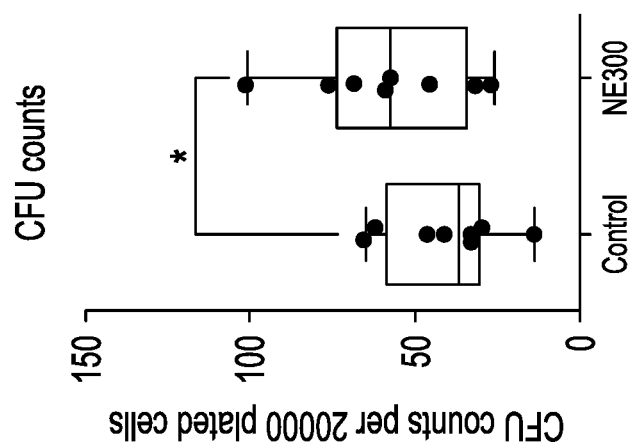

As neural crest-conditioned media increased the HSC-like cell frequency in iPS-to-blood differentiation culture, we further tested if a known neural crest-derived factor, norepinephrine (NE), could similarly induce hematopoietic cells in our differentiation assay We applied 2 different concentrations of NE, 10 µM (NE10) and 300 µM (NE300) at day 10 and day 12, followed by analysis of the hematopoietic output at day 14 NE300 significantly increased the HSC-like phenotype in total viable cells, see FIG. 2B. This effect was similar across several human ES and iPS cell lines (FIG. 2C). We analyzed the hematopoietic cells and observed that blood and progenitor fraction were unchanged after NE treatment (FIG. 2D, E), while the HSC-like cells were specifically and significantly upregulated (FIG. 2F). When the obtained cells were plated in methylcellulose to assess the colony-forming unit (CFU) frequency, we observed a significant increase in colony formation by the hematopoietic cells generated with NE300 (FIG. 2G), although the distribution of colony types was not affected (FIG. 2H). In order to determine whether the observed increase in HSC immunophenotype was due to increased emergence of immature hematopoietic cells from endothelium, we assessed the effect of NE on the frequency of endothelial precursors identified in our culture system as CD34high CD90high (FIG. 2I). We observed a trend for an increase in this fraction when NE was added at 300 µM (FIG. 2J), similar effect observed across multiple cell lines (FIG. 2K).

Discussion

In the present study, using human pluripotent stem cell differentiation assay, we asked if the signals from neural crest stem cells may provide the missing signals required to elicit the maturation/expansion of bona fide HSCs with long-term engraftment ability. For this purpose, we generated neural crest stem cells from pluripotent stem cells using an established protocol. Using NC conditioned media in our iPS differentiation system, we observed an increase in the immature hematopoietic progenitor fraction harboring an HSC immunophenotype. Subsequently, application of norepinephrine, the most abundant neurotransmitter produced by the neural crest-derived cells of the peripheral nervous system, produced similar effect, suggesting NC-mediated signaling to be playing a role in the observed upregulation of HSC-like cells.

Catecholamines secreted by the developing peripheral nervous system were recently shown to regulate HSC emergence in the AGM region, where a catecholamine-deficient Gata3−/−phenotype showed reduced levels of HSC emergence in the AGM and was rescued using adrenergic receptor agonists. Though the expression of ADRB2 on the nascent HSCs was evaluated, mechanisms of ADRB2-meduated signaling remain elusive.

The positive effect of norepinephrine for in vitro generation of cells with HSC immunophenotype, indicates that during vitro recapitulation of human development using human pluripotent stem cells, adrenergic signaling appears to be a relevant pathway modulating human hematopoietic development. Taking advantage of our in vitro differentiation settings and given that norepinephrine signaling through the ADRB2 is a known activator of cAMP, the effects of norepinephrine provides a mechanism of why norepinephrine is able to increase hematopoietic cell output.

Example 2

Introduction

Hematopoietic stem cells (HSC) replenish hematopoiesis throughout the lifetime of an individual and can be transplanted into patients to treat malignant and non-malignant blood disorders. The need to develop an alternative source of HSCs to matched adult donors, such as HSCs generated from pluripotent stem cells, requires increased understanding of the mechanisms of HSC development. During development, the first hematopoietic cells emerge from hemogenic endothelium in the embryonic aorta-gonad-mesonephros (AGM) region through endothelial-to-hematopoietic transition (EHT). The concurrence of neural crest stem cells in the AGM region coincides with the time of HSC emergence, suggesting a link between neural crest/catecholamines and hematopoietic development. Recently, catecholamine signaling has been reported to regulate HSC emergence in the AGM region, as the deletion of GATA binding protein 3 (GATA3), a crucial regulator of catecholamine production, compromised HSC development, which could be rescued with administration of catecholamine derivatives. However, the mechanism of catecholamine signaling, through its second messenger, cyclic AMP (3'-5'-cyclic adenosine mono phosphate), and its downstream signaling pathways had not previously been critically evaluated in the context of hematopoietic development. In the adult hematopoietic system, a parallel situation to the hematopoietic developmental context exists. Catecholamines and sympathoadrenergic innervation of the bone marrow (BM) niche regulates HSC mobilization and migration of catecholamine receptor-expressing hematopoietic stem and progenitors cells. Together, these studies during developmental hematopoiesis and adult hematopoiesis provided evidence for neural regulation of hematopoietic cells and establish catecholamine-mediated signaling as a key component of the hematopoietic program.

Activation of specific G-protein coupled receptors by catecholamines, as well as neurotransmitters, growth factors and hormones activates the cyclic AMP signaling pathway, followed by cell-type dependent responses mediated by cAMP effectors Protein Kinase A (PKA) and Exchange proteins activated by cAMP (Epac). Epac have been shown to modulate endothelial cell remodeling, enhances endothelial cell adhesion, and regulate the integrity of endothelial cell junctions, however, the role of Epac in EHT was previously unknown. Cyclic AMP-mediated regulation of adult hematopoiesis was previously emphasized in studies showing that: cAMP increases C—X—C chemokine receptor type 4 (CXCR4) expression and motility of hematopoietic progenitors, HSCs from Gsα-deficient mice do not engraft and Gsα-deficient osteocytes alter the BM niche, leading to defective hematopoiesis. In human hematopoietic cells, Prostaglandin E2 (PGE2)-mediated cAMP activation enhances human cord blood engraftmen. Recently, cAMP was shown to regulate hematopoietic emergence and homing in studies where cAMP was upregulated by adenosine in zebrafish and mouse, by PGE2 in zebrafish and mouse, and by shear stress in murine AGM. However, the role and mechanism of cAMP signaling, as mediated through PKA and Epac, in regulating human developmental hematopoiesis has not been adequately studied, and no study has been performed on the role of cAMP in the human hematopoietic developmental context. We have shown that human pluripotent stem cells (hPSC)-derived HSClike cells possess lymphoid and myeloid differentiation ability, a key feature of HSCs, and thus that hPSC, including human embryonic stem cells (hESC) and induced pluripotent stem cells (iPSC), provide an ideal in vitro model to recapitulate human hematopoietic development. Recent studies have functionally demonstrated an endothelial precursor to blood (hemogenic endothelium) from hPSC differentiation cultures, further establishing hPSCs as a suitable model to study human hematopoietic cell development. However, the signals regulating EHT in human hematopoiesis previously remained undefined. Additionally, for functional transplantable HSCs, it is vital to reduce reactive oxygen species (ROS) and oxidative stress, as reduced ROS is crucial for HSC functionality. As cAMP-mediated regulation of human hematopoietic cell emergence remains elusive, we set out to investigate the role of cAMP signaling in hPSCderived hematopoietic emergence. Here we provide evidence that cAMP induction during hPSC-to-hematopoietic differentiation increases the frequency of cells with HSC-like surface phenotype and increases the colony forming unit potential. Furthermore we demonstrate that cAMP regulation of human HSC-like cell emergence is dependent on the cAMP-Epac signaling axis. We propose that this cAMP-mediated increase in HSC-like cells is in part coupled to cAMP-mediated mitigation of oxidative burden and increasing hematopoietic cell function.

Experimental Procedures

Human Pluripotent Stem Cell Culture

Human iPSC line RB9-CB1 derived from cord blood endothelial cells was cultured on irradiated mouse embryonic fibroblasts (MEFs) in Dulbecco's Modified Eagle Medium:Nutrient Mixture F-12 (DMEM/F12) supplemented with 20% KnockOut-serum replacement (KOSR), 2 mM L-glutamine, 0.1 mM non-essential amino acids, 0.1 mM 2-mercaptoethanol and 10 ng/ml basic fibroblast growth factor, all from Thermo Fischer Scientific Inc. (Waltham, Mass., USA). The cells were incubated in a humidified incubator at 370 C and 5% CO2.

Embryoid Body Formation and Hematopoietic Differentiation

Embryoid bodies (EBs) were prepared after incubating the pluripotent stem cell colonies with 2 mg/ml Dispase (Thermo Fischer Scientific Inc.), followed by gentle pipetting. The detached colonies were washed twice with 20% KOSR containing DMEM/F12, before plating in ultra low-adherence suspension culture dishes (Corning Inc., Corning, N.Y., USA) to form EBs for 8 days. During suspension culture, MesoTotal™ HPC/HSC Differentiation System (Primorigen Biosciences, Madison, Wis., USA) was used to specify the EBs towards mesoderm commitment. At day 8, EBs were plated on 0.08 µg/mm2 Matrigel™ (BD Biosciences, Franklin Lakes, N.J., USA) and further differentiation towards hematopoietic cells was carried out till day 14 in MesoTotal medium.

Application of fresh medium and treatment with 10 µM Forskolin (Stemgent, Cambridge, Mass., USA), 500 µM IBMX (3-isobutyl-1-methylxanthine, Santa Cruz Biotechnology, Dallas, Tex., USA) was carried out at day 10 and day 12 of differentiation. To inhibit PKA and Epac, 50 µM PKA inhibitor (Rp-8-CPT-cAMPS) and 20 µM Epac inhibitor (ESI-09) (both from BIOLOG Life Science Institute, Bremen, Germany) were used (20 min pretreatment followed by cAMP induction) on day 10 and day 12 of differentiation and the cells were analyzed on day 14. To analyze hemogenic endothelium, PKA and Epac were inhibited on day 6 and day 8 and the cells were analyzed on day 10. The distance between center of an EB and outer edge of its cellular spread was analyzed using ImageJ (developed at the National Institutes of Health, USA).

Colony Formation Assay

After 14-day hPSC-to-hematopoietic differentiation, the differentiated hematopoietic cells were plated (1×104 cells/ 9.5 cm2) in Methocult™ H4230 (STEMCELL Technologies Inc., Vancouver, BC, Canada) supplemented with 2.5 µg/ml human Stem Cell Factor (SCF), 2.5 µg/ml human Interleukin-3 (IL3), 5 µg/ml human Granulocyte-macrophage colony-stimulating factor (GM-CSF) and 500 U/ml Erythropoietin (EPO), all recombinant human cytokines from PeproTech (Rocky Hill, N.J., USA). After 12 days, hematopoietic colonies were scored microscopically to evaluate various CFU phenotypes.

Flow Cytometry

To analyze surface markers, cells harvested using TrypLE™ Select (Thermo Fischer Scientific Inc.) were labeled with primary antibodies for 30 min at 40 C. The following fluorophore-conjugated antibodies were used: CD43-FITC, CD45RA-V450, CD73-PE, anti-VE-cadherin-Percp-Cy5.5 (all from BD) and CD34-PE.Cy7, CD38-APC, CD90-PE, CXCR4-BV421 (all from BioLegend, San Diego, Calif., USA). After incubation with the antibodies for 30 min, cells were washed, resuspended in 2% fetal bovine serum (Thermo Fischer Scientific Inc.) containing phosphate buffered saline and acquired with BD FACSCanto™ (BD Biosciences). To detect oxidative stress, CellROX® Deep Red (Life Technologies) was used according to the manufacturer's instructions. For live/dead cell discrimination, 7-amino-actinomycin D (BD Biosciences) was applied to the cells before acquisition. Dot plots were derived from gated events based on size and scatter characteristics and doublet-exclusion, fluorescent Minus One (FMO) controls were used to identify gating boundaries. Acquired events were analyzed using FlowJo software (Ashland, Oreg., USA). RNA Isolation and qRT-PCR Total RNA from cells was extracted using RNeasy® Micro Kit (Qiagen Inc., Valencia Calif., USA) and 500 ng of total RNA was reverse transcribed to cDNA using SuperScript® III reverse transcriptase (Life Technologies) according to the manufacturer's instructions.

Quantitative PCR was performed with gene-specific primers (Table 1) using SYBR® GreenER™ qPCR SuperMix (Life Technologies) in 7900HT Fast Real-Time PCR system (Life Technologies), and the relative expression to housekeeping gene β-ACTIN was analyzed by the comparative CT method. Statistical Analysis Statistical analysis was performed using GraphPad Prism (GraphPad Software, San Diego, Calif., USA). Quantitative data represents mean±standard error of mean (S.E.M), unless otherwise stated, 'n' represents the number of biological replicates. For statistical evaluation, student's t-test (twotailed) was used, statistical significance is indicated by *, $p<0.05$, , $p<0.01$, *, $p<0.001$, ****, $p<0.0001$, n.s., not significant.

TABLE 1

| | |
|---|---|
| NFE2L2.F | TGACAATGAGGTTTCTTCGGCT |
| NFE2L2.R | GACTGGGCTCTCGATGTGAC |
| SOD2.F | GCTCCGGTTTTGGGGTATCTG |
| SOD2.R | GCGTTGATGTGAGGTTCCAG |
| SOD1.F | GGTGGGCCAAAGGATGAAGAG |
| SOD1.R | CCACAAGCCAAACGACTTCC |
| GPX2.F | GGTAGATTTCAATACGTTCCGGG |
| GPX2.R | TGACAGTTCTCCTGATGTCCAAA |
| CAT.F | TGTTGCTGGAGAATCGGGTTC |
| CAT.R | TCCCAGTTACCATCTTCTGTGTA |
| GSR.F | TTCCAGAATACCAACGTCAAAGG |
| GSR.R | GTTTTCGGCCAGCAGCTATTG |
| P38MAPKα.F | GCTTCAGCAGATTATGCGTCTG |
| P38MAPKα.R | GTTTCTTGCCTCATGGCTTGG |
| P38MAPKδ.F | AAGCTGAGCCGACCCTTTC |
| P38MAPKδ.R | CCAATGACGTTCTCATGCTGC |
| P38MAPKγ.F | ACATGAGAAGCTAGGCGAGGA |
| P38MAPKγ.R | GGCAGCGTGGATATACCTCAG |
| β-ACTIN.F | CCCCGCGAGCACAGAG |
| β-ACTIN.R | ATCATCCATGGTGAGCTGGC |

Figure 3A:
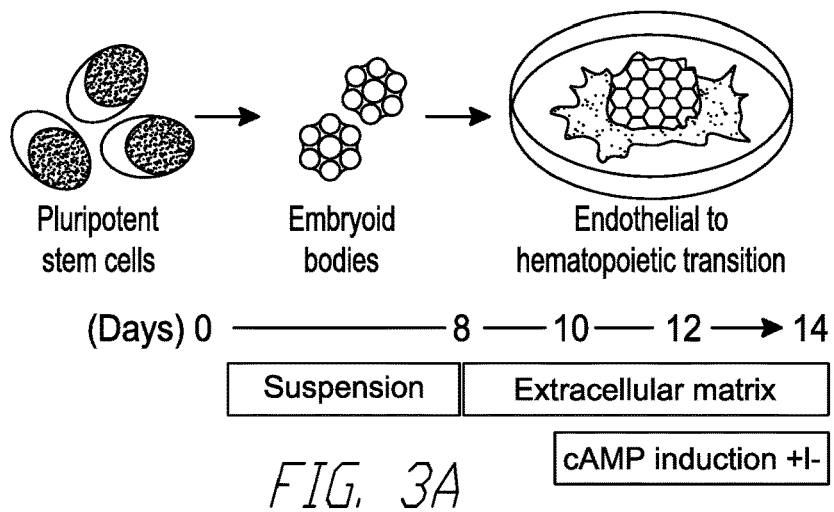
FIG. 3: Cyclic AMP Induction Increases HSC-like Frequency During hPSC-to-Hematopoietic Differentiation. A) Conditions and timeline applied to differentiate hPSCs towards mesoderm commitment and hematopoietic differentiation; B) Flow cytometric analysis of hematopoietic cells at day 14 of differentiation. Representative flow cytometry plots (biexponential axis) of cells cultured in control medium (Mesototal), and cells treated with Forskolin, IBMX, or Forskolin+IBMX are shown; C) Percent of the hematopoietic surface phenotypes indicated in (B). Data represents mean±S.E.M. of three independent experiments. Statistical analysis was performed using the t-test. Significance is shown compared to the control setting. *, p<0.05, ***, p<0.001, n.s., not significant; D) Frequency of the putative HSC-like cells (in viable fraction) is shown. Data represents mean±S.E.M. of three independent experiments. Statistical analysis was performed using the t-test. Significance is shown compared to the control setting. *, p<0.05, n.s., not significant; E) Total CFU numbers after 12-day colony-forming unit (CFU) assay of differentiated hematopoietic cells treated with Forskolin, IBMX and Forskolin+IBMX. The CFU distribution of 3 independent experiments is shown as total number of colonies. CFU-G (granulocyte), CFU-M (macrophage), CFU-E (erythroid), CFU-GM (granulocyte/macrophage). Statistical analysis was performed using the t-test. Significance is shown compared to the control setting. *, p<0.05, , p<0.01, *, p<0.001; F) Cell numbers obtained per well (per $1 \times 10^4$ seeded cells) after CFU assay are shown. Data represents mean±S.E.M. of three independent experiments. Statistical analysis was performed using the t-test. Significance is shown compared to the control setting. , p<0.01, *, p<0.001, n.s., not significant. See also FIGS. 5 and 6.
Figure 3B:
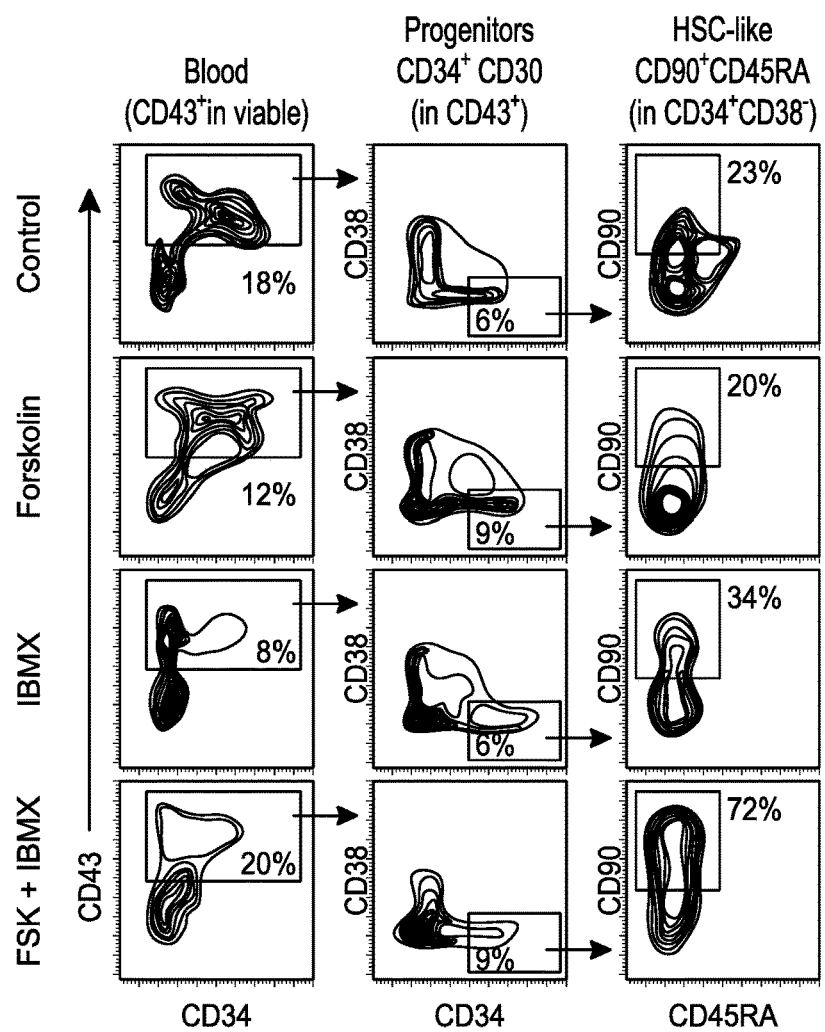
Figure 3C:
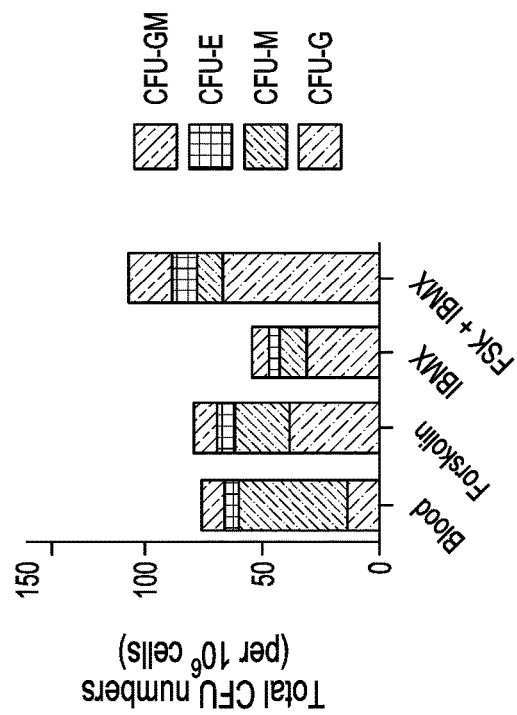
Figure 3D:
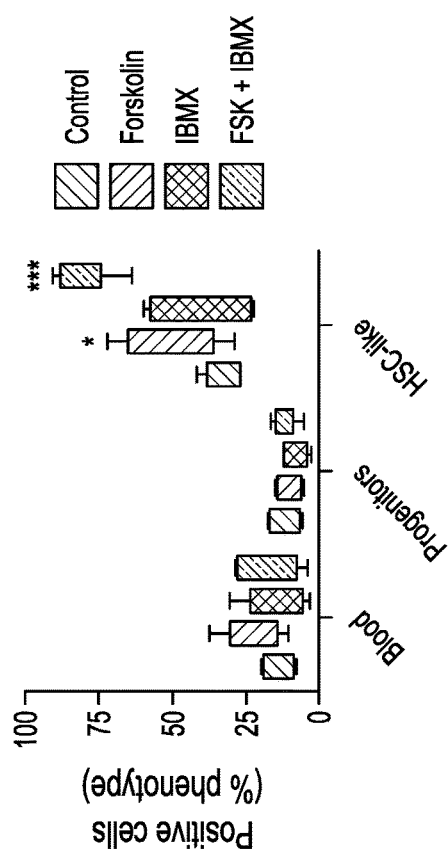
Figure 3E:
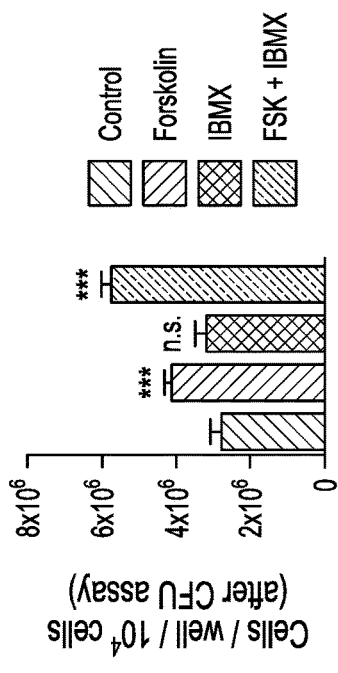
Figure 3F:
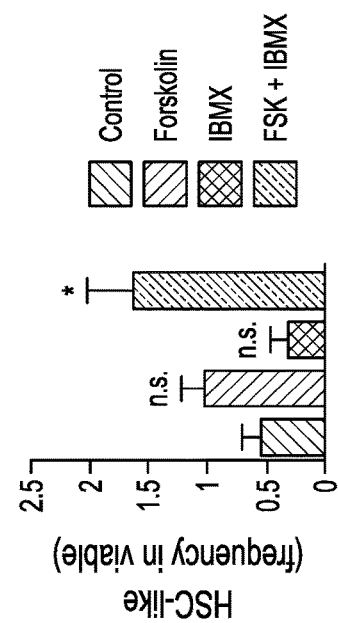
Figure 4:
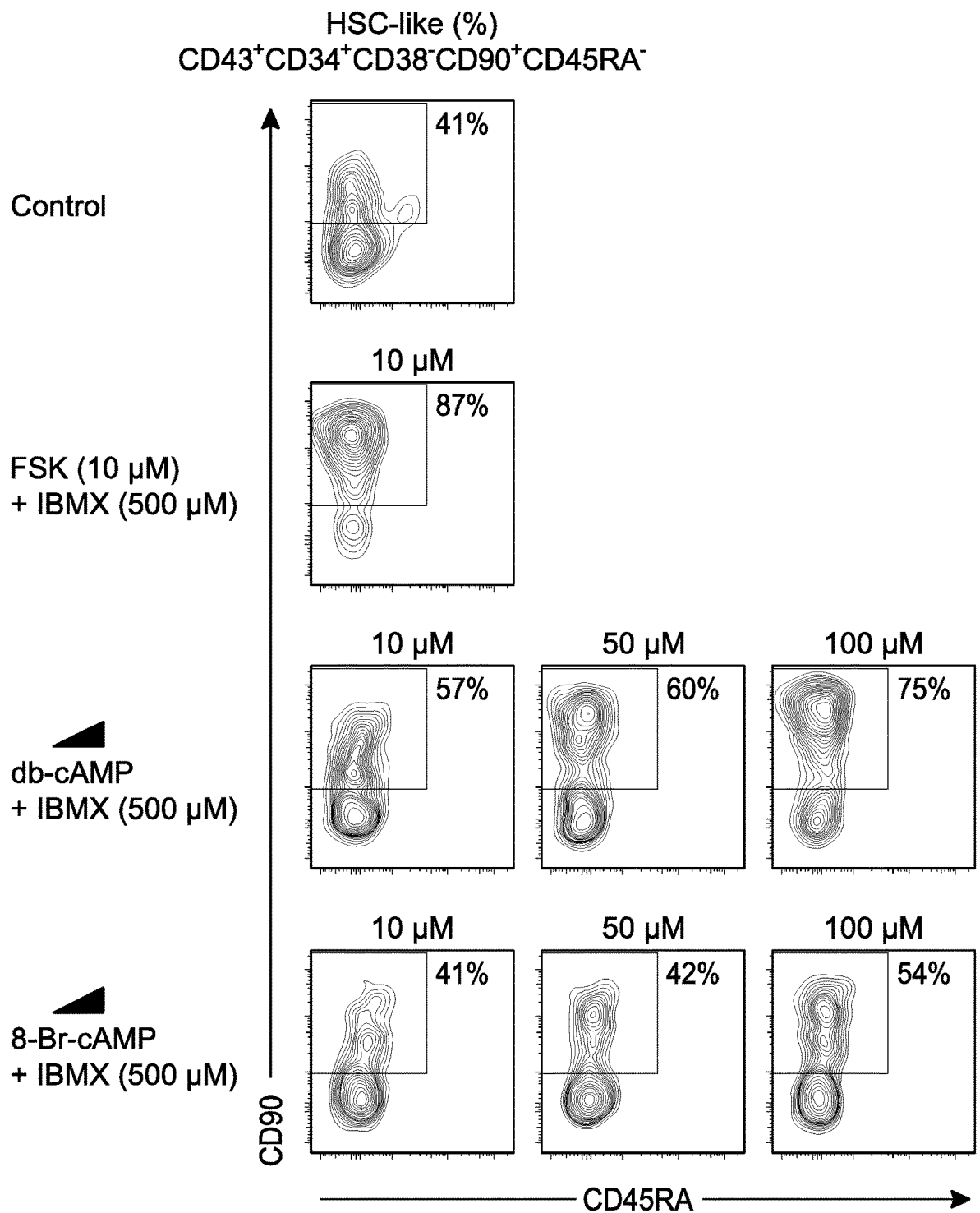
FIG. 4: Synthetic cell-permeable cAMP analogs db-cAMP and 8-Br-cAMP increase HSC-like phenotype, although a 10-fold higher concentration is required as compared to Forskolin. Flow cytometric pots (biexponential axis) showing the HSC-like surface phenotype in hPSC-derived hematopoietic cells on day 14, a representative experiment is shown. FMO control, fluorescence minus-one (staining control).
Figures 5A, 5B:
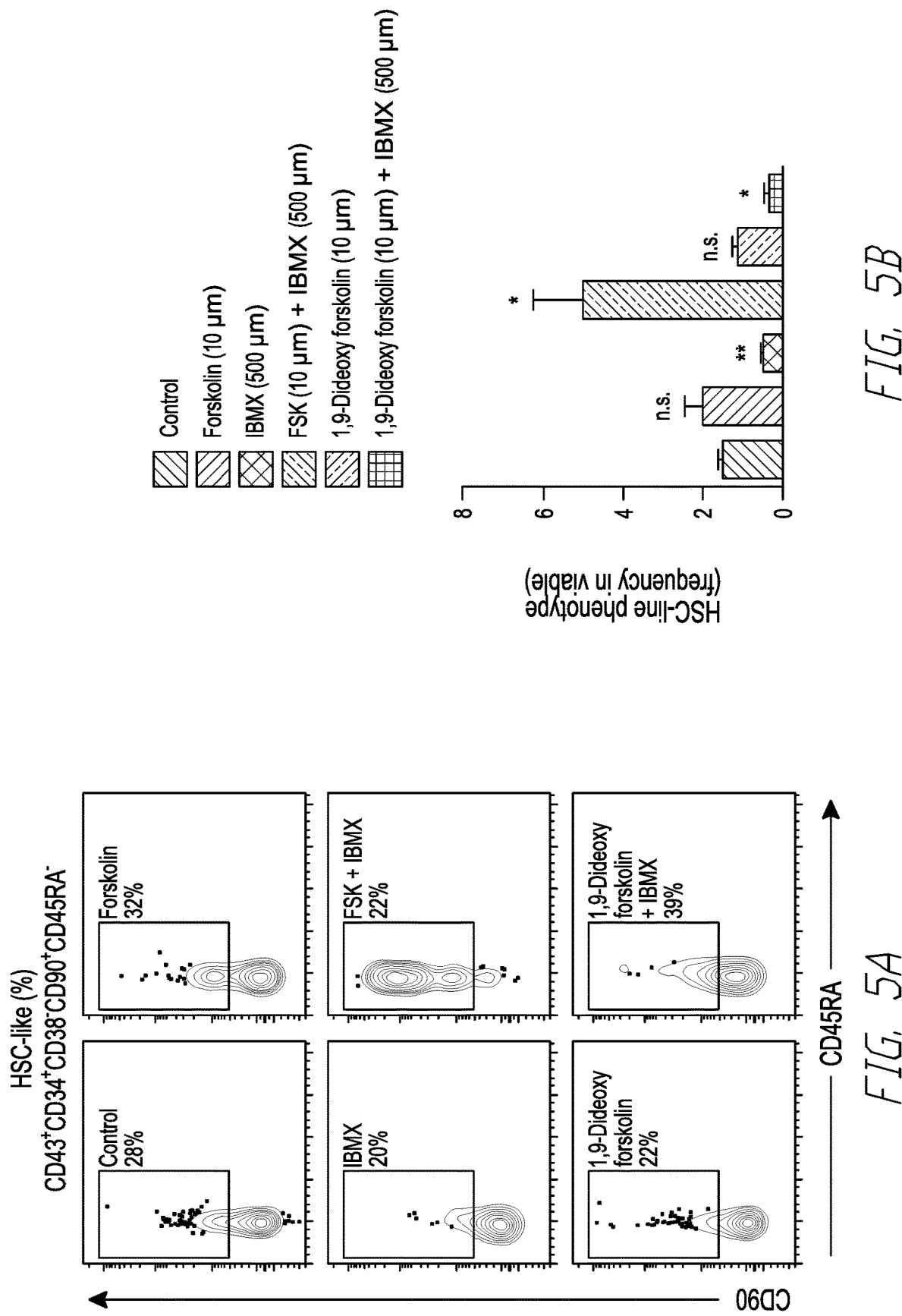
FIG. 5: Effect of cAMP induction using Forskolin+IBMX is specific for upregulation of the HSC-like phenotype, as 1,9-dideoxy Forskolin, a negative control of Forskolin, cannot induce HSC-like phenotype. A) Flow cytometric plots (biexponential axis) showing HSC-like surface phenotype on d14, a representative experiment is shown. B) Quantification of HSC-like (frequency in viable) is shown. Data represents mean±SEM, n=2. Statistical analysis was performed using the t-test. Significance is shown compared to the control setting. *, p<0.05, **, p<0.01, n.s., not significant.
Figures 6A, 6B:
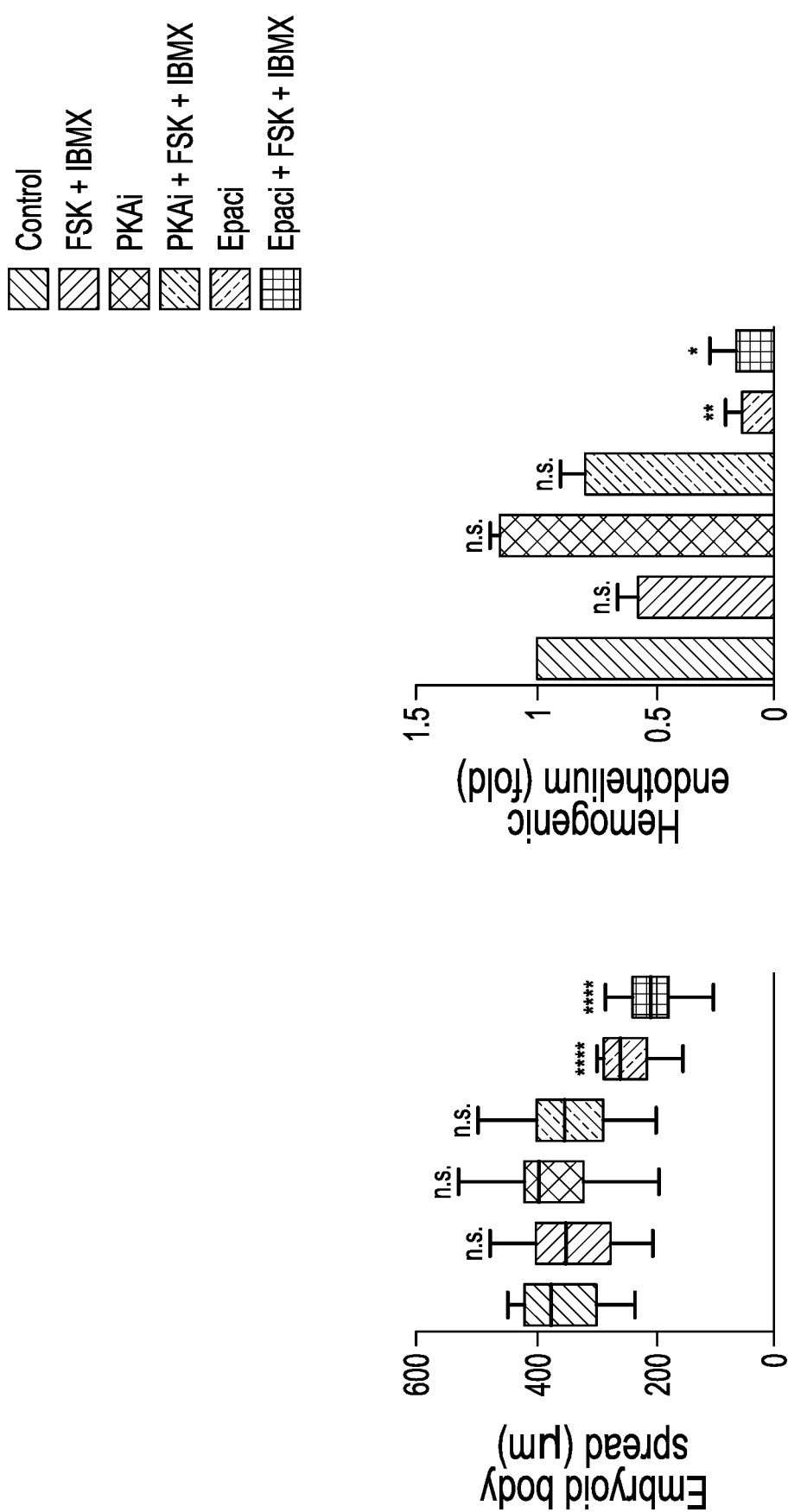
FIG. 6: Cyclic AMP-mediated HSC-like upregulation occurs through the camp-Epac axis. A) quantification of the distance between center of EB and outer edge of the cellular spread is shown. Data represents mean±S.E.M. of 100 EB's from 3 independent experiments. Statistical analysis was performed using the t-test. Significance is shown compared to the control setting. ****, p<0.0001, n.s., not significant; B) Assessment of hemogenic endothelial (CD43−CD34+ CXCR4−CD73− VEcad+) phenotype, after Forskolin+IBMX mediated cAMP induction and PKA or Epac inhibition (PKAi, Epaci) with or without Forskolin+IBMX is shown. Data represents mean±S.E.M. of three independent experiments; mean fold change respective to control condition is shown. Statistical analysis was performed using the t-test. Significance is shown compared to the control setting. *, p<0.05, **, p<0.01, n.s., not significant; C) Representative flow cytometry plots (biexponential axis) showing the CD43+ blood cells and HSC-like cells generated after Forskolin+IBMX mediated cAMP induction and PKA or Epac inhibition (PKAi, Epaci), with or without Forskolin+IBMX; D) Quantification of HSC-like frequency in viable as indicated in (C). Data represents mean±S.E.M. of three independent experiments. Statistical analysis was performed using the t-test. Significance is shown compared to the control setting. *, p<0.05, , p<0.01, n.s., not significant. See also FIG. 7**.
Figure 6C:
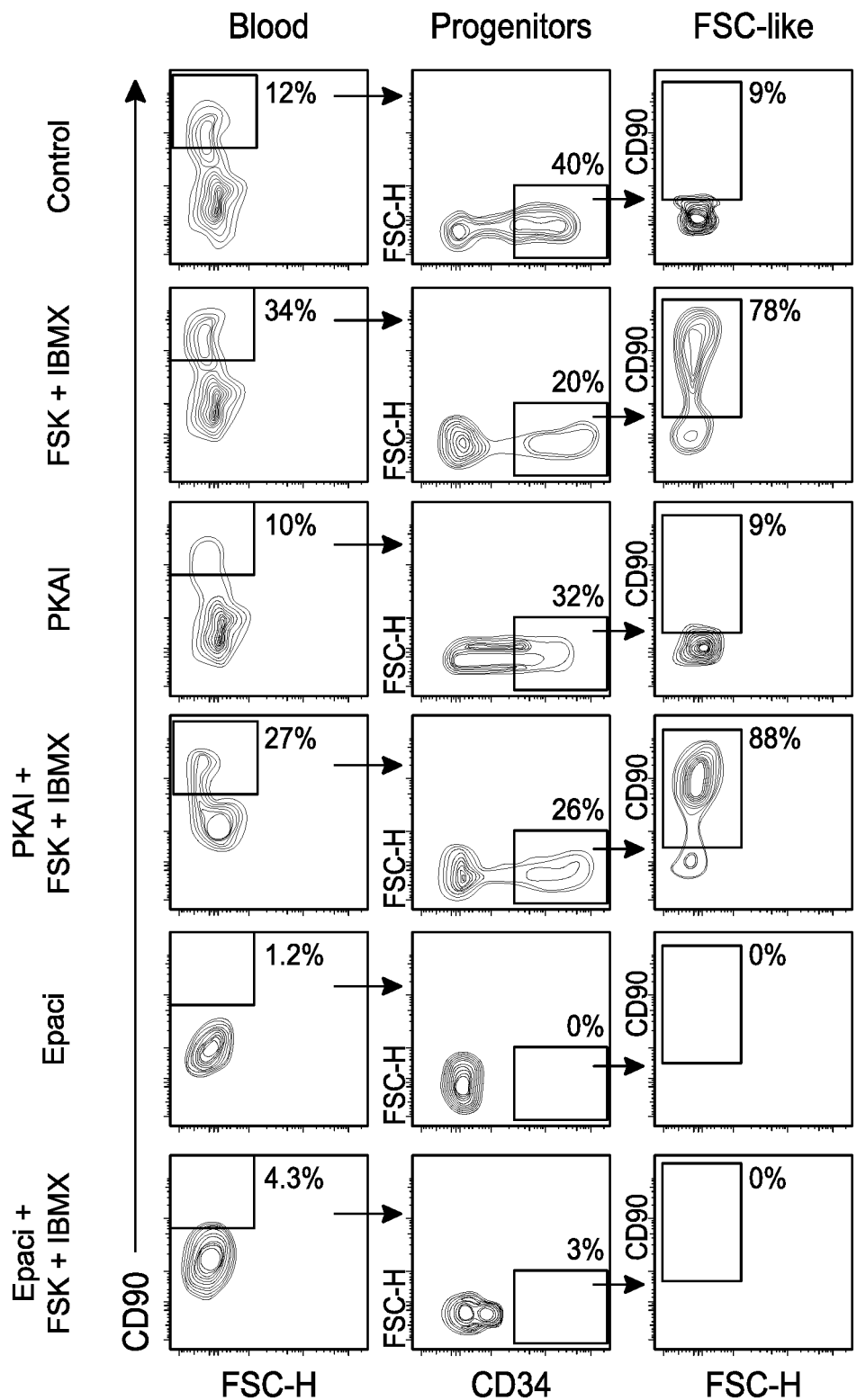
Figure 6D:
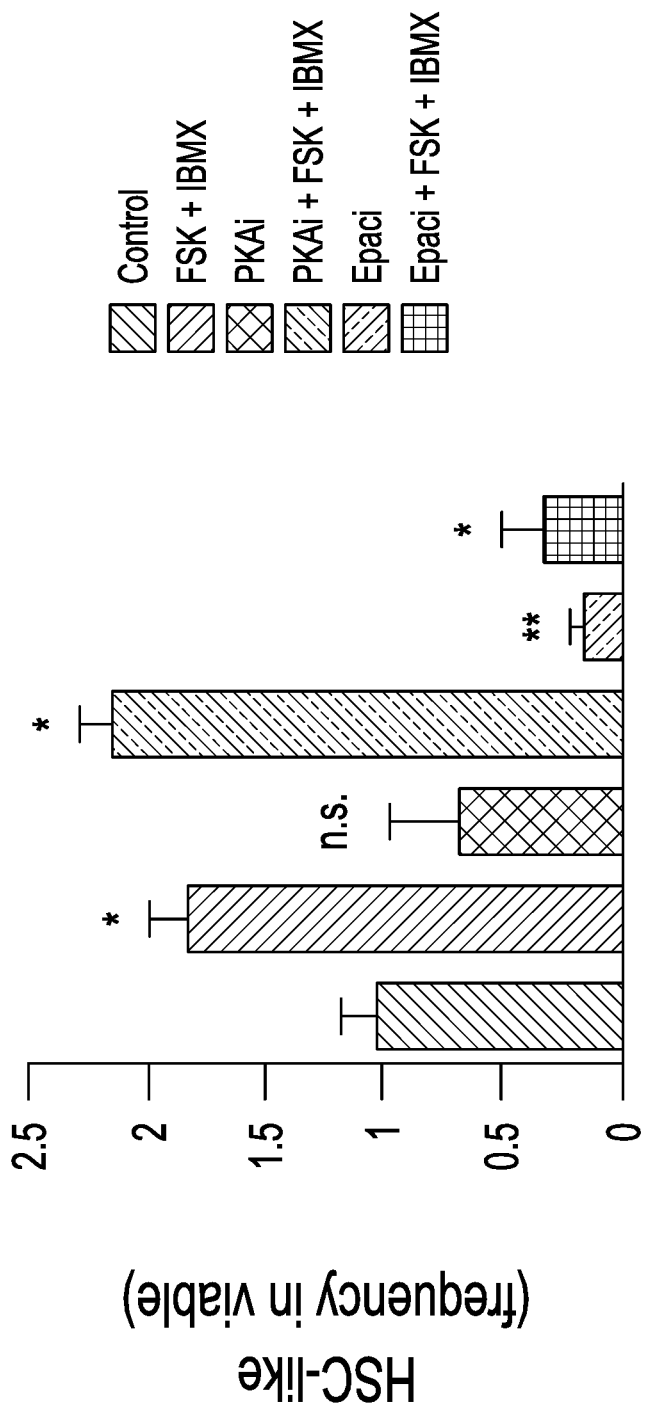
Figure 7:
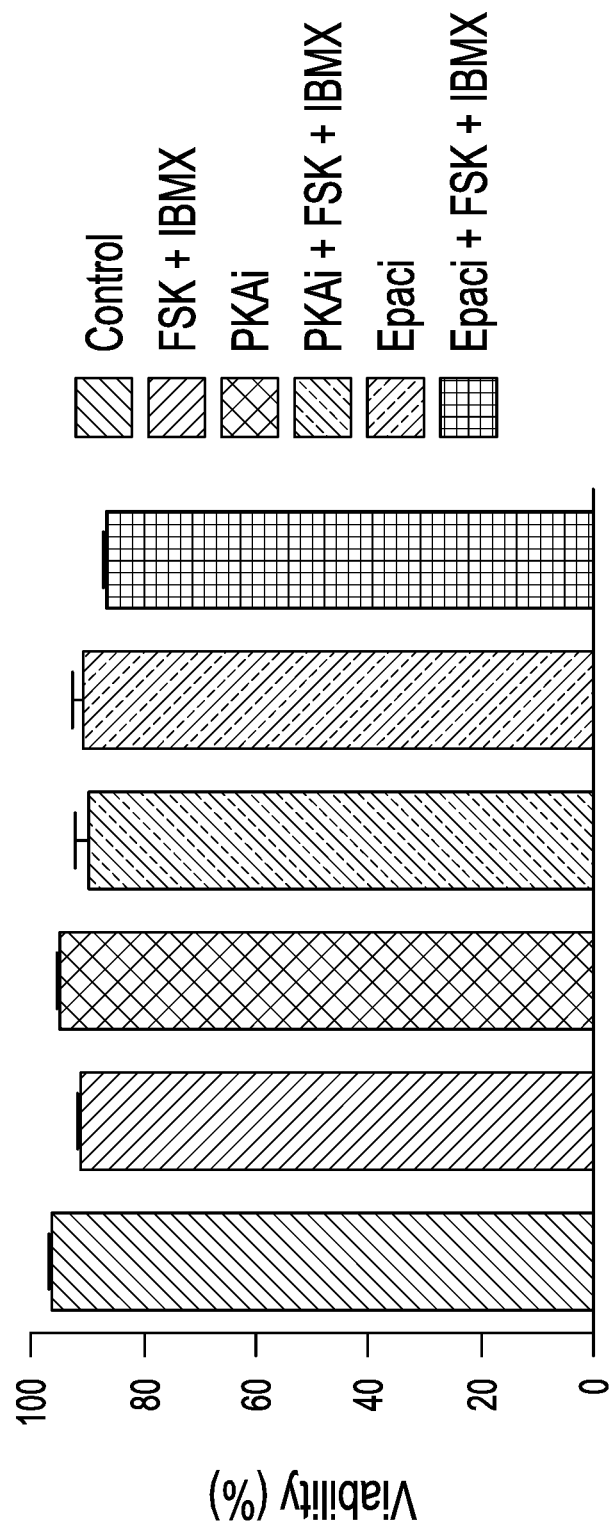
FIG. 7: Cellular viability was not compromised after PKA or Epac inhibition. Viability of cells is shown, as determined by flow cytometry. Live cells were quantified (7AAD−), data represents mean±SEM, n=2.

Results
Cyclic AMP Induction Increases Frequency of HSC-Like Cells in hPSC-Derived Hematopoietic Progenitors In order to assess the role of cAMP signaling in human hematopoietic development, we differentiated hPSCs using our previously described protocol (Ronn et al., 2015) whereby mesoderm-biased embryoid bodies were plated onto extracellular matrix allowing for adherence and expansion of hemogenic endothelium, to generate hematopoietic cells (FIG. 3A). To elevate intracellular cAMP, we applied a combination of Forskolin and IBMX from day 10. Forskolin specifically increases intracellular cAMP levels by activating the catalytic subunit of adenylyl cyclase. 3-isobutyl-1-methylxanthine (IBMX) is a phosphodiesterase (PDE) inhibitor that specifically prevents PDE-mediated dephosphorylation of cAMP to AMP. Thus combining Forskolin with IBMX elevates intracellular cAMP, by increasing cAMP production and preventing its dephosphorylation. FACS analysis of the hPSC-derived hematopoietic cells revealed that cAMP induction with Forskolin+IBMX significantly increased the numbers and frequency of our previously described HSC-like cells (CD43+CD34+CD38−CD90+CD45RA−) (FIG. 3B, C, D). To confirm that the upregulation of HSC-like cells was specifically due to increased cAMP levels, we used two different synthetic cAMP analogs dibutyryl-cAMP and 8-Br-cAMP to elevate intracellular cAMP during hPSC-tohematopoietic differentiation. Both cAMP analogs upregulated the HSC-like phenotype (FIG. 4). Also, in order to rule out any unspecific effects of Forskolin, we used 1,9-Dideoxyforskolin, an inactive analog of Forskolin that does not activate adenylyl cyclase. We observed that HSC-like phenotype was induced only with Forskolin+IBMX, not with 1,9-Dideoxyforskolin+IBMX (FIG. 5A, B), thus verifying the specificity of Forskolin-mediated effects through cAMP. Cyclic AMP induction with Forskolin+IBMX resulted in higher numbers of total colonies in colony-forming unit (CFU) assay (FIG. 3E) and significantly increased cell numbers resulting from the colony assay (FIG. 3F), as compared to non-induced control. Assessment of the differentiation capacity of hematopoietic cells in CFU assay showed an increase in granulocyte CFUs (CFU-G) and erythroid colonies, while the numbers of macrophage CFUs (CFU-M) were decreased (FIG. 3E). Together, these data show that elevation of intracellular cAMP upregulates hPSC-derived HSC-like surface phenotype, increases the CFU potential of hematopoietic progenitors and also alters the distribution of colony types, favoring mixed, granulocyte and erythroid colonies at the expense of macrophage colonies. Cyclic AMP Signaling through the Epac Axis is Required for HSC-Like Cell Generation from Endothelial Cell Intermediate Intracellular cAMP downstream effectors PKA and Epac influence cellular functions by regulating the activation of various transcription factors and signaling molecules. We set out to elucidate the mechanism of cAMP-mediated upregulation of phenotypic HSC-like cells during hPSC-to-hematopoietic differentiation. Inhibition of Epac in the absence or presence of Forskolin+IBMX reduced the radial spreading of adherent endothelial-like cells, while PKA inhibition did not have any effect (FIG. 6A). Cell viability after PKA and Epac inhibition was similar to controls at 90-95% (FIG. 7 FIG. 7). As bona fide hematopoietic cells were previously reported to emerge from such endothelial spread, we evaluated the effect of Epac inhibition on the frequency of the previously described hemogenic endothelium phenotype cells (CD43−CD34+CXCR4−CD73−Vecad+). Epac inhibition in the absence or presence of Forskolin+IBMX decreased the hemogenic endothelial fraction (FIG. 6B). Epac inhibition reduced the hematopoietic cell generation efficiency as assessed using the pan-hematopoietic marker CD43 and consequently led to the decreased frequency of HSC-like cells (FIG. 6C, D). Inhibition of PKA on the other hand had no negative effect on hemogenic endothelium, blood emergence and HSC-like cells (FIG. 6B, C, D). These results indicate that cAMP-Epac axis plays a pivotal role in the emergence of blood/HSC-like cells, by regulating hemogenic endothelial cell function during in vitro differentiation of pluripotent stem cells.

Figure 8B:
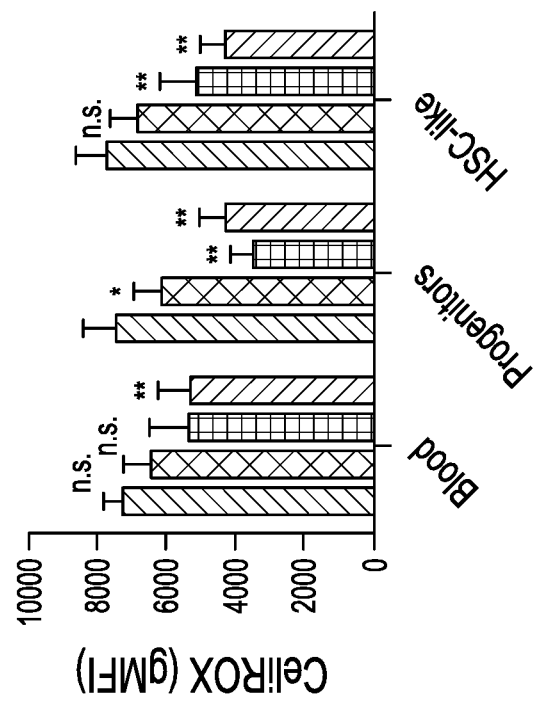
FIG. 8: Cyclic AMP induction reduces oxidative stress and induces CXCR4 in hPSC-derived hematopoietic cells. A) Flow cytometric analysis for detection of reactive oxygen species (ROS) in differentiated hPSC-to-hematopoietic cells at day 14 of differentiation. Representative flow cytometry plots (biexponential x-axis) show ROS levels in the hematopoietic surface phenotypes. FMO control, fluorescence minus-one (staining control); B) Quantification of geometric mean fluorescence intensity (gMFI) of CellROX dye as indicated in (A). Data represents mean±S.E.M. of three independent experiments. Statistical analysis was performed using the t-test. Significance is shown compared to the control setting. *, p<0.05, **, p<0.01, n.s., not significant; C) qRT-PCR expression analysis of the indicated redox state-regulating genesin PSC-derived hematopoietic cells. Relative expression of each gene to housekeeping gene ACTB (β-ACTIN) was calculated and mean fold change respective to control condition (set at one) is shown. Data represents mean±S.E.M. of two independent experiments. Statistical analysis was performed using the t-test. Significance is shown compared to the control setting. *, p<0.05, **, p<0.01, n.s., not significant. D) qRT-PCR expression analysis of the indicated p38MAPK-related genes in PSC-derived hematopoietic cells. Relative expression of each gene to housekeeping gene ACTB (β-ACTIN) was calculated and mean fold change respective to control condition (set at one) is shown. Data represents mean±S.E.M. of two independent experiments. Statistical analysis was performed using the t-test. Significance is shown compared to the control setting. *, p<0.05, **, p<0.01, n.s., not significant; E) Expression of CXCR4 across indicated hematopoietic surface phenotypes is shown. Data represents mean±S.E.M. of three independent experiments. Statistical analysis was performed using the t-test. Significance is shown compared to the control setting. *, p<0.05, , p<0.01, *, p<0.001, n.s., not significant; F) Expression of CXCR4 in HSC-like surface phenotype (ROS-low fraction) is shown. Data represents mean±S.E.M. of three independent experiments. Statistical analysis was performed using the t-test. Significance is shown compared to the control setting. *, p<0.001, n.s., not significant. See also FIG. 9**.
Figure 8A:
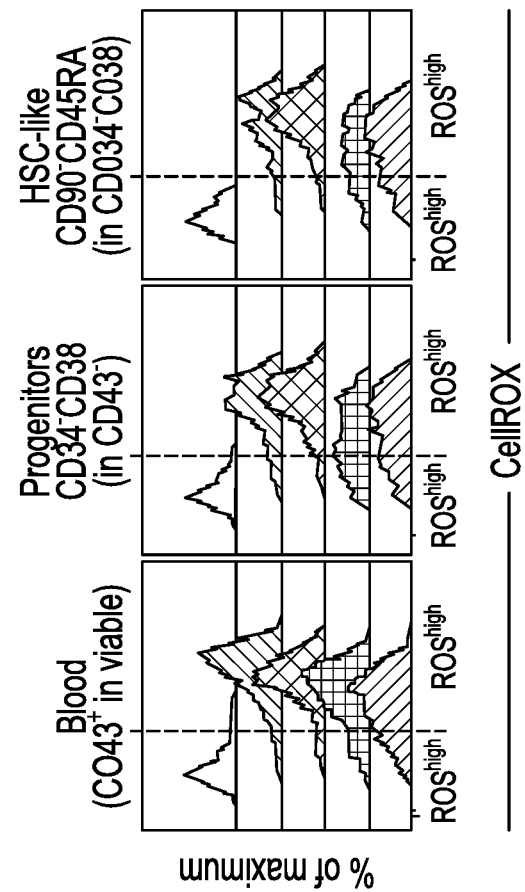
Figure 8C:
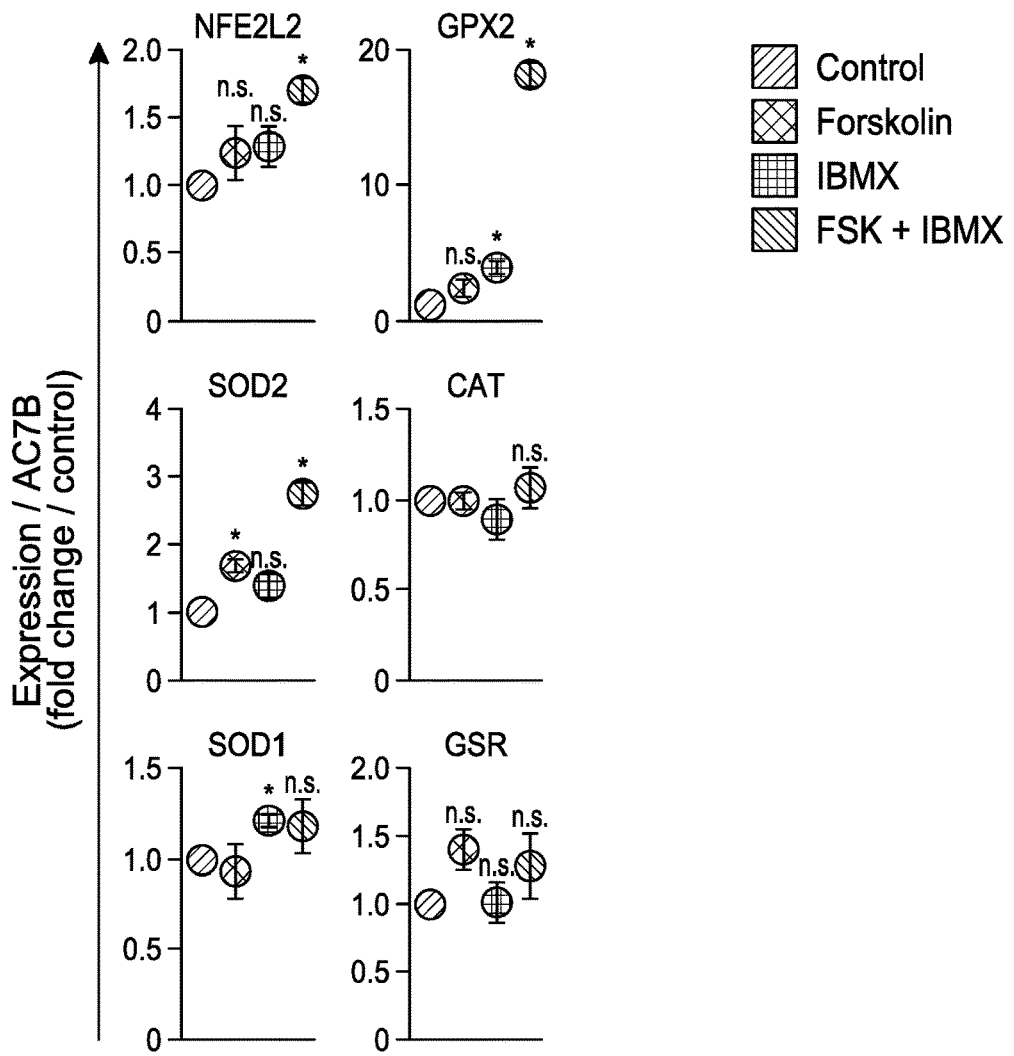
Figure 8D:
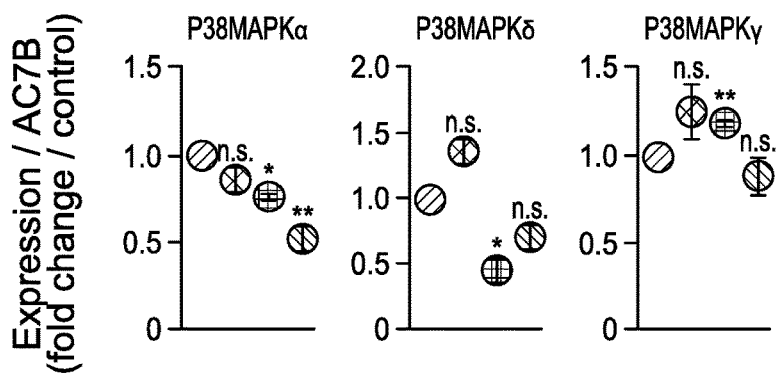
Figure 8F:
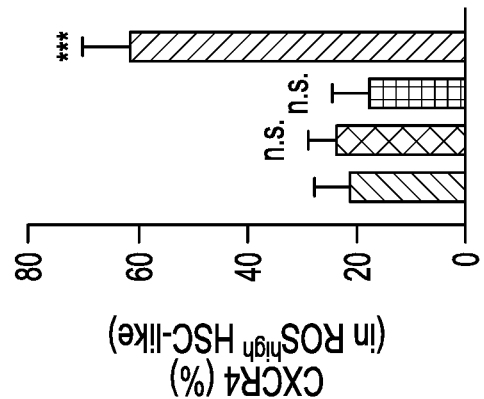
Figure 8E:
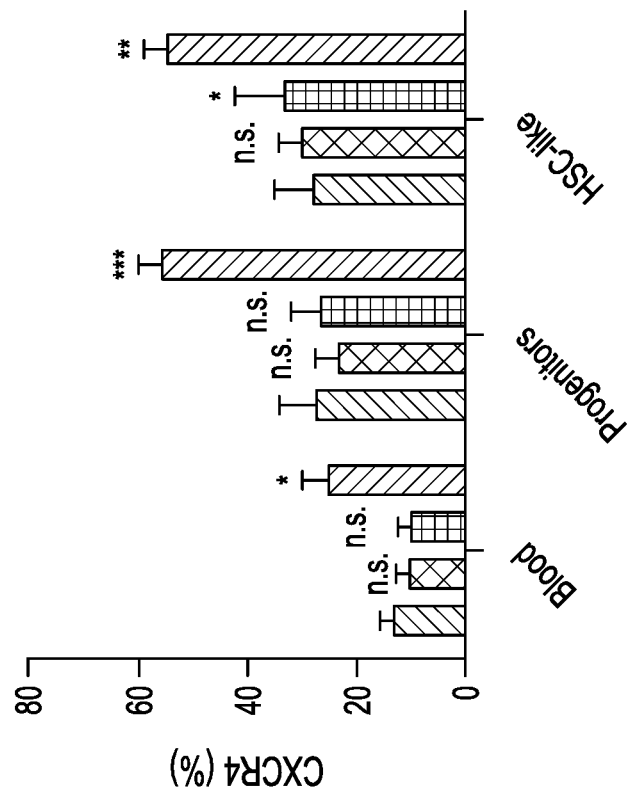
Figure 9:
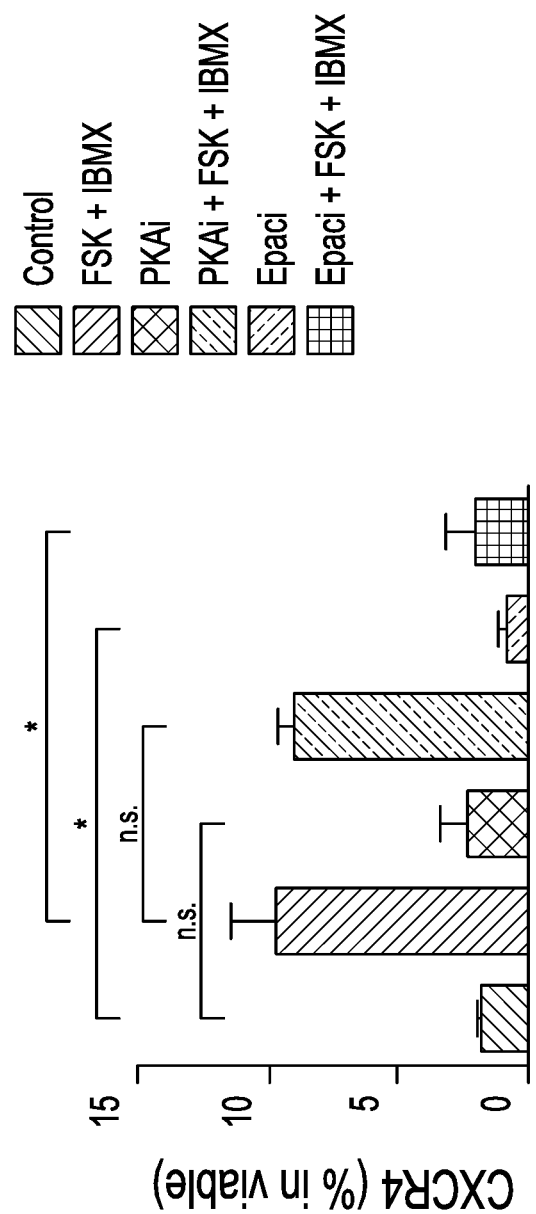
FIG. 9: Cyclic AMP-Epac axis regulates CXCR4 expression. Assessment of CXCR4 expression levels, after Forskolin+IBMX mediated cAMP induction and PKA or Epac inhibition (PKAi, Epaci) with or without Forskolin+IBMX, is shown. Data represents mean±SEM, n=2. Statistical analysis was performed using the t-test. *, p<0.05.

Cyclic AMP Induction Reduces Oxidative Stress and Induces CXCR4 Upregulation in hPSC-Derived Hematopoietic Cells The deleterious effects of elevated ROS and its ensuing oxidative damage on the function of mammalian HSCs were previously known. As cAMP induction decreased the prevalence of macrophages in our system (FIG. 3E) and as cAMP elevation coupled with PDE inhibition is known to promote immune homeostasis, we rationalized that cAMP induction with Forskolin+IBMX might mitigate ROS burden in our hPSC-to-hematopoietic differentiation system, thus protecting the HSC-like cells from ROS-mediated effects mentioned above. Analysis of ROS levels showed that cAMP induction decreased the ROS levels in hPSCderived hematopoietic cells, compared to the control setting (FIG. 8A). Cyclic AMP induction along with PDE inhibition (Forskolin+IBMX), and protecting endogenously available cAMP with PDE inhibition alone (IBMX), significantly lowered the ROS levels in various hematopoietic phenotypes, including the HSC-like cells (FIG. 8B), thus indicating reduced oxidative stress of these hematopoietic cellular fractions. The decreased ROS level after cAMP induction prompted us to determine the status of genes that regulate the redox state of cells and thus help to reduce the oxidative stress. Transcriptional analysis of the redox state regulating genes in hPSC-derived hematopoietic cells showed that Nuclear factor (erythroid-derived 2)-like 2 (NFE2L2) was upregulated after cAMP induction with Forskolin+IBMX (FIG. 8C). NFE2L2 is a global regulator of the oxidative stress response as it binds to antioxidant response element (ARE) in the upstream promoter region of several antioxidative genes and initiates their transcription, thus initiating the mitigation of ROS-induced oxidative stress in the cells. In our system, NFE2L2 upregulation after cAMP induction was in concert with the upregulation of antioxidant genes, such as superoxide dismutase (SOD1, SOD2), glutathione peroxidase (GPX2) (18-fold increase), catalase (CAT) and glutathione S-reductase (GSR) (FIG. 8C). Stress conditions activate p38 Mitogen-Activated Protein Kinases (p38MAPK) (Raingeaud et al., 1995). ROS/stress-mediated p38MAPK activation leads to HSC self-renewal defects and reduced HSC long-term repopulation potential. Thus we analyzed the levels of stress-activated p38 pathway components P38-MAPKα, δ, and □ and found that cAMP induction generally reduced the levels of these p38MAPK isoforms (FIG. 8D), indicative of reduced stress. Together these data indicate that cAMP induction with Forskolin+IBMX upregulated anti-oxidant defense mechanisms and down-regulated stressactivated genes, thus creating a redox balance in our system, and along with cAMP-mediated signals, led to the upregulation of HSC-like cells (FIG. 3D) and increased CFU potential (FIG. 3E). The chemokine receptor CXCR4 is pivotal for retaining quiescent HSCs in the BM niche, as well as for HSC homing to BM. Given that cAMP is known to increase CXCR4 expression in adult HSCs, we analyzed CXCR4 levels in hPSC-derived hematopoietic cells. Analysis of CXCR4 expression revealed that cAMP induction with Forskolin+IBMX enhanced CXCR4 expression across various hematopoietic surface phenotypes, including the HSC-like fraction (FIG. 8E). Importantly, CXCR4 expression was enhanced in the ROSlow HSC-like surface phenotype upon treatment with Forskolin+IBMX (FIG. 8F). Interestingly, Epac inhibition, with or without cAMP induction, reduced CXCR4 expression as compared to the control (FIG. 9), demonstrating that cAMP-Epac axis is responsible for the cAMP mediated upregulation of CXCR4. Together, these findings show that cAMP induction reduced oxidative burden by creating a redox-state balance in hPSC-derived hematopoietic cells and upregulated CXCR4 in the HSC-like surface phenotype, both essential for HSC functionality.

Discussion

Using hPSCs as an in vitro model to recapitulate human hematopoetic cell emergence and development, our findings demonstrate that cAMP and signaling through its Epac axis are important factors for the generation of HSC-like cells and the hemogenic endothelium from which the first hematopoietic cells arise. We provide evidence that cAMP is a crucial second messenger molecule regulating the in vitro specification of hPSC-derived HSC-like cells having effects both on the precursors of blood as well as on the blood cells themselves whereby the hematopoietic progenitors and HSC-like cells have properties in line with features desired from adult donor derived blood sources, and with increased frequency and numbers of these de novo generated blood cells compared to de novo generated blood cells without cAMP induction. cAMP induction also mitigated oxidative stress, created redox-state balance, and enhanced CXCR4 expression in hPSCderived hematopoietic cells. Because of the importance of low ROS levels in maintaining the function of repopulating human HSCs, the identification of cAMP-mediated ROS reduction is critical to further developing hPSC differentiation system in order to better mimic the in vivo HSC development. We suggest that the presence of mature immune cells might elevate ROS activity in our differentiation system. The reduction in macrophage numbers, following cAMP induction, agrees with cAMP-mediated redox-state balance, leading to decreased ROS levels. ROS reduction was in concert with the increase of antioxidant gene response and decrease in the p38 stress pathway components. These findings suggest that cAMP induction imparts important functional properties to the derived hematopoietic cells, as low oxidative stress and high CXCR4 expression are properties of HSCs with long-term transplantation potential. Our findings on the role of cAMP signaling in hPSC-derived hematopoietic cell specification are in agreement with recent reports describing the pivotal role of cAMP signaling in mouse and zebrafish hematopoietic system. These studies demonstrated that cAMP activation by fluid shear stress in the murine system or by adenosine signaling in the zebrafish hematopoietic system, instructs hematopoietic specification. However the mechanism that was suggested in these studies was through cAMP-PKA axis signaling. In our in vitro model of human hematopoietic development, we show that by inhibiting the downstream effectors of cAMP signaling, PKA and Epac, only Epac signaling is required for hematopoietic emergence during hPSC differentiation towards the hematopoietic lineage. Notwithstanding the critical evaluation of Epac axis that was lacking in the previous reports, we cannot exclude an inter-species variation of this mechanism, and the HSC specification mechanism in zebrafish and murine system might be divergent from human hematopoietic development. Cyclic AMP-mediated Epac upregulation has been reported to reorganize cortical actin and enhance vascular endothelial cadherin-mediated cell adhesion, leading to decreased endothelial cell permeability and enhanced endothelial barrier function. Developmentally, in the early embryo, hematopoietic cells (including cells with the potential to form HSCs) emerge from hemogenic endothelium in the AGM region through EHT. Epac being one of the downstream effectors of cAMP that regulates endothelial cell-cell adhesion, and the requirement of endothelial cells for EHT during hematopoietic emergence, together suggest a novel link between endothelial cell junctions and EHT for subsequent hematopoietic cell emergence. In our Epac inhibition experiments, we observed impairment in hemogenic endothelium specification, reduced blood emergence and decreased numbers of HSC-like cells, thus demonstrating the critical role of Epac signaling in the specification of human hemogenic endothelium and hPSC-derived HSC-like cells. Collectively, our findings show that cAMP regulates human HSC generation during in vitro human hematopoiesis. By demonstrating the role of cAMP-Epac axis in blood and HSC emergence, our study provides new insights in understanding the previously unknown role of the cAMP-signaling component in human hematopoietic development. Taken together, these findings advance our current understanding of hematopoietic developmental mechanisms, towards developing transplantable hematopoietic cells for therapeutic purposes.

The above-described embodiments have been provided by way of example, and the methods and cells described herein are not limited to these examples. Multiple variations and modification to the disclosed embodiments will occur, to the extent not mutually exclusive, to those skilled in the art upon consideration of the foregoing description. Additionally, other combinations, omissions, substitutions and modifications will be apparent to the skilled artisan in view of the disclosure herein. Accordingly, the methods and cells disclosed herein are not intended to be limited by the disclosed embodiments, but are to be defined by reference to the appended claims. Those skilled in the art will recognize, or be able to ascertain using no more than routine experimentation, many equivalents to the specific embodiments of the methods and cells described herein. Such equivalents are intended to be encompassed by the following claims.

What is claimed is:

1. A method of producing hematopoietic cells, comprising:
   obtaining cells that are capable of generating hematopoietic cells;
   culturing said cells under conditions that specify them towards the hematopoietic lineage and/or through hematopoietic lineages;
   further culturing said cells in a medium that comprises an activator of cyclic adenosine monophosphate (cAMP) or cAMP-Epac axis, wherein Epac refers to Exchange proteins activated by cAMP, thereby obtaining hematopoietic cells; and
   selectively removing macrophages during culturing of said cells in the medium.

2. The method of claim 1, further comprising culturing or expanding the population of the cells prior to or after culturing said cells under conditions that specify them towards the hematopoietic lineage and/or through hematopoietic lineages.

3. The method of claim 1, wherein embryoid bodies are not formed.

4. The method of claim 1, wherein the activator of cAMP reduces oxidative stress on the cells.

5. The method of claim 4, wherein oxidative stress is further reduced by either controlling the environmental oxygen level, or culturing the cells in the presence of redox state modifiers.

6. The method of claim 3, wherein the activator of cAMP enhances expression of the CXCR4 protein on the surface of the cells.

7. The method of claim 1, wherein the cells are selected from the group consisting of pluripotent stem cells, embryonic stem cells, induced pluripotent stem cells (iPSC), directly reprogrammed somatic cells with hemogenic potential, hemogenic endothelial cells, precursors of hematopoietic cells, and any combination thereof.

8. The method of claim 1, wherein the cAMP and/or cAMP-Epac axis activator is selected from the group consisting of forskolin, IBMX, norepinephrine, epinephrine, salmeterol, isoproterenol, db-cAMP, 8-Br-cAMP, Bucladesine, 6-Bnz-cAMP, cAMPS -Sp, triethylammonium salt, N6-Monobutyryladenosine 3':5'-cyclic monophosphate sodium salt, 8-Bromoadenosine 3',5'-cyclic monophosphate, Adenosine 3',5'-cyclic monophosphate, CW008 (4-Fluoro-N-[5-fluoro-6-(5-methoxypyrazolo[1,5-a]pyridin-3-yl)-1H-pyrazolo[3,4-b]pyridin-3-yl]benzamide), Cholera toxin, Prostaglandins, or any combination thereof.

9. The method of claim 1, wherein the activator of the cAMP-Epac axis is a direct activator of Epac.

10. The method of claim 1, wherein the medium excludes an inhibitor of Epac.

11. The method of claim 1, wherein the medium further comprises an inhibitor of macrophage development.

12. A method of producing hematopoietic cells, comprising:
   obtaining cells that are capable of generating hematopoietic cells;
   culturing said cells under conditions that specify them towards the hematopoietic lineage and/or through hematopoietic lineages;
   furthur culturing said cells in a medium that comprises an activator of cyclic adenosine monophosphate (cAMP) or cAMP-Epac axis, wherein Epac refers to Exchange proteins activated by cAMP, thereby obtaining hematopoietic cells;
   reducing oxidative stress by either controlling the environmental oxygen level or culturing the cells in the presence of redox state modifiers; and
   wherein embryoid bodies are not formed.

13. The method of claim 12, further comprising culturing or expanding the population of the cells prior to or after culturing said cells under conditions that specify them towards the hematopoietic lineage and/or through hematopoietic lineages.

14. The method of claim 12, wherein the activator of cAMP reduces oxidative stress on the cells.

15. The method of claim 12, wherein the activator of cAMP enhances expression of the CXCR4 protein on the surface of the cells.

16. The method of claim 12, wherein the cells are selected from the group consisting of pluripotent stem cells, embryonic stem cells, induced pluripotent stem cells (iPSC), directly reprogrammed somatic cells with hemogenic potential, hemogenic endothelial cells, precursors of hematopoietic cells, and any combination thereof.

17. The method of claim 12, wherein the cAMP and/or cAMP-Epac axis activator is selected from the group consisting of forskolin, IBMX, norepinephrine, epinephrine, salmeterol, isoproterenol, db-cAMP, 8-Br-cAMP, Bucladesine, 6-Bnz-cAMP, cAMPS-Sp, triethylammonium salt, N6-Monobutyryladenosine 3':5'-cyclic monophosphate sodium salt, 8-Bromoadenosine 3',5'-cyclic monophosphate, Adenosine 3',5'-cyclic monophosphate, CW008 (4-Fluoro-N-[5-fluoro-6-(5-methoxypyrazolo[1,5-a]pyridin-3-yl)-1H-pyrazolo[3,4-b]pyridin-3-yl]benzamide), Cholera toxin, Prostaglandins, or any combination thereof.

18. The method of claim 1, wherein the activator of the cAMP-Epac axis is a direct activator of Epac.

19. The method of claim 12, wherein the medium excludes an inhibitor of Epac.

20. The method of claim 12, wherein the medium further comprises an inhibitor of macrophage development.

* * * * *